US011292778B2

(12) United States Patent
Sletten et al.

(10) Patent No.: US 11,292,778 B2
(45) Date of Patent: Apr. 5, 2022

(54) HETEROCYCLYL POLYMETHINE IR CHROMOPHORES

(71) Applicant: The Regents of the University of California, Oakland, CA (US)

(72) Inventors: Ellen M. Sletten, Los Angeles, CA (US); Emily D. Cosco, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/619,770

(22) PCT Filed: Jun. 5, 2018

(86) PCT No.: PCT/US2018/036099
§ 371 (c)(1),
(2) Date: Dec. 5, 2019

(87) PCT Pub. No.: WO2018/226720
PCT Pub. Date: Dec. 13, 2018

(65) Prior Publication Data
US 2020/0140404 A1 May 7, 2020

Related U.S. Application Data

(60) Provisional application No. 62/515,459, filed on Jun. 5, 2017.

(51) Int. Cl.
| | |
|---|---|
| *C07D 311/60* | (2006.01) |
| *C07D 311/92* | (2006.01) |
| *C07D 405/14* | (2006.01) |
| *C07D 491/14* | (2006.01) |
| *C07D 491/16* | (2006.01) |
| *A61K 45/06* | (2006.01) |

(52) U.S. Cl.
CPC .......... *C07D 311/60* (2013.01); *C07D 311/92* (2013.01); *C07D 405/14* (2013.01); *C07D 491/14* (2013.01); *C07D 491/16* (2013.01); *A61K 45/06* (2013.01)

(58) Field of Classification Search
CPC .. C07D 311/60; C07D 311/92; C07D 405/14; C07D 491/14; C07D 491/16; A61K 45/06
See application file for complete search history.

(56) References Cited

U.S. PATENT DOCUMENTS

| | | | |
|---|---|---|---|
| 4,714,667 A | 12/1987 | Sato et al. | |
| 5,166,041 A * | 11/1992 | Murofushi | C09D 11/50 430/108.2 |
| 5,214,164 A | 5/1993 | Drexhage et al. | |
| 5,262,549 A | 11/1993 | Telfer et al. | |
| 6,221,574 B1 | 4/2001 | Missfeldt | |
| 9,862,682 B2 | 1/2018 | Zhang et al. | |
| 2002/0115862 A1 | 8/2002 | Czerney et al. | |
| 2004/0162423 A1 | 8/2004 | Czerney et al. | |
| 2009/0200167 A1 | 8/2009 | Kratzmeier et al. | |
| 2009/0252687 A1 | 10/2009 | Cooper | |
| 2013/0039858 A1* | 2/2013 | Brown | C09B 23/0041 424/9.3 |
| 2015/0322078 A1 | 11/2015 | Hermanson et al. | |
| 2020/0140404 A1 | 5/2020 | Sletten et al. | |

FOREIGN PATENT DOCUMENTS

| | | |
|---|---|---|
| EP | 0362387 A1 | 4/1990 |
| EP | 0438123 A2 | 7/1991 |
| EP | 0841189 A1 | 5/1998 |
| EP | 3118201 A1 | 1/2017 |
| JP | S60 252346 A | 12/1985 |
| JP | 3341141 B2 | 11/2002 |
| JP | 2003176270 A | 6/2003 |
| JP | 2004/083799 A | 3/2004 |
| JP | 2007298642 A | 11/2007 |
| JP | 2016113503 A | 6/2016 |
| WO | WO-2014/035712 A1 | 3/2014 |
| WO | WO-2014/081419 A2 | 5/2014 |
| WO | WO-2015042202 A1 | 3/2015 |
| WO | WO-2015/066290 A1 | 5/2015 |
| WO | WO-2016/081813 A1 | 5/2016 |
| WO | WO-2017/025968 A1 | 2/2017 |
| WO | WO-2017027721 A1 | 2/2017 |
| WO | WO-2018/187295 A1 | 10/2018 |
| WO | WO-2018/226720 | 12/2018 |
| WO | WO-2020/118116 A1 | 6/2020 |

OTHER PUBLICATIONS

Kudinova et al., (10) Khimiya Geterotsiklicheskikh Soedinenii 1319-23 (1993) (Year: 1993).*
Atchison et al., "Iodinated Cyanine Dyes: A New Class of Sensitisers for; use in NIR Activated Photodynamic Therapy (PDT)," Chemical Communications, 53(12): 2009-2012 (2017).
Gandioso et al., "High Photostability in Nonconventional Coumarins with Far-Red/NIR Emission through Azetidinyl Substitution," The Journal Of Organic Chemistry, 83(19): 11519-11531 (2018).
Guo et al., "Preliminary structure-activity relationship study of heptamethine indocyanine dyes for tumor-targeted imaging," Journal of Innovative Optical Health Sciences, 6(01): 1350003 (2013).
Henary et al., "Synthesis and applications of benzothiazole containing cyanine dyes," Heterocyclic Communications, 19(1): 1-11 (2013).
International Search Report and Written Opinion for International Patent Application No. PCT/US2019/064790 dated Mar. 17, 2020.
Kovalska et al., "6,6'-Disubstituted benzothiazole trimethine cyanines—new fluorescent dyes for DNA detection," Spectrochimica Acta Part A: Molecular and Biomolecular Spectroscopy, 65(2): 271-277 (2006).
Li et al., "An Efficient 1064 nm NIR-II Excitation Fluorescent Molecular Dye for Deep-Tissue High-Resolution Dynamic Bioimaging," Angewandte Chemie International Edition, 57(25): 7483-7487 (2018).

(Continued)

*Primary Examiner* — Timothy R Rozof
(74) *Attorney, Agent, or Firm* — Foley Hoag LLP; David P. Halstead; Lucas Watkins

(57) ABSTRACT

The present disclosure provides SWIR-active small molecule polymethine dyes with improved properties for use in optical imaging, photothermal therapy, photodynamic therapy, and SWIR-promoted drug delivery.

18 Claims, 6 Drawing Sheets

(56) References Cited

OTHER PUBLICATIONS

Li et al., "Small Molecule Near-Infrared Boron Dipyrromethene Donors for Organic Tandem Solar Cells," Journal Of The American Chemical Society, 139(39): 13636-13639 (2017).
Mikubayeva et al., "Combined Sensitisation of Benzaldehyde Diphenylhydrazones: Effect of Hydrazone Structure on Sensitization Efficiency," Eurasian ChemTech Journal, 6(2): 133-138 (2004).
Shi et al., "Review on near-infrared heptamethine cyanine dyes as theranostic agents for tumor imaging, targeting, and photodynamic therapy," Journal of Biomedical Optics, 21(5): 050901 (2016).
Thimsen et al., "Shortwave-infrared (SWIR) emitters for biological; imaging: a review of challenges and opportunities," Nanophotonics, 6(5): 1043-1054 (2017).
Yarmoluk et al., "Optimized Dyes for Protein and Nucleic Acid Detection," Advanced Fluorescence Reporters in Chemistry and Biology III, 113:161-199 (2011).
U.S. Appl. No. 16/619,770, Pending.
Extended European Search Report for EP Application No. 18813396.1 dated Feb. 16, 2021.
Extended European Search Report for EP Application No. EP 18781895 dated Feb. 16, 2021.
U.S. Appl. No. 16/499,700, Pending.
Blackburn et al., "302. Reactions of flavylium salts with dimethylaniline and malonic acid," Journal of the Chemical Society (Resumed), 1957:1573-1576 (1957).
CAS Registry No. 169336-73-6 (Oct. 27, 1995).
CAS Registry No. 219991-09-0 (Feb. 25, 1999).
Chen et al., "Development of Unique Xanthene-Cyanine Fused Near-Infrared Fluorescent Fluorophores with Superior Chemical Stability for Biological Fluorescence Imaging," Chemistry A European Journal, 21(2): 733-745 (2015).
Detty et al,. "Heavy Atom Effects in Tellurapyrylium Dyes Useful in Photodynamic Therapy and Catalytic Generation of H2O2," Phosphorus, Sulfur, and Silicon and the Related Elements, 67(1-4): 383-404 (1992).
Gadjev et al., "Near-infrared absorbing asymmetric trimethinecyanine dyes containing benz[c,d]indolium and pyrylium end groups," Dyes and Pigments, 17(2): 153-162 (1991).
Gavrilyuk et al., "Pyrolocyanines. 17. Symmetrical flavylocyanines based on methoxysubstituted 4-methylflavylium salts," Chemistry of Heterocyclic Compounds, 19(3): 243-247 (1983).
Gavrilyuk et al., "Pyrylocyanines. 18. Unsymmetrical flavylocyanines on the basis of methoxysubstituted 4-methylflavylium salts," Chemistry of Heterocyclic Compounds, 19(9): 948-950 (1983).
Kamel et al., "Dibenzoxanthylium salts-III: Studies on 9-methylene-3,4,5,6-dibenzoxanthene and 3,4,5,6-dibenzoxanthylomethines," Tetrahedron, 20(3): 483-489 (1964).
Katritzsky et al., "Comprehensive Heterocyclic Chemistry," Elsevier Science, Par 2.02 titled "Reactivity of Six-membered Rings", scheme 19, compound 77; Par. 2.23 titled "Pyrans and Fused Pyrans: (ii) Reactivity", compound 119 (1984).
Mishra et al., "Cyanines during the 1990s: A Review," Chemical Reviews, 100(6): 1973-2012 (2000).
Shandura et al., "Substituted xanthylocyanines. II. Pyroninocyanines," Dyes and Pigments, 66(3): 171-177 (2005).
Shindy et al., "Fundamentals in the chemistry of cyanine dyes: A review," Dyes and Pigments, 145: 505-513 (2017).
Usama et al., "Optimized Heptamethine Cyanines for Photodynamic Therapy," ACS Applied Bio Materials, 1(4): 1195-1205 (2018).
Vasyluk et al., "Breaking of symmetrical charge distribution in xanthylocyanine chromophores detecting by their absorption spectra," Journal of Molecular Structure, 990(1-3): 6-13 (2011).
Wei et al., "Design of NIR Chromenylium-Cyanine Fluorophore Library for "Switch-ON" and Ratiometric Detection of Bio-Active Species In Vivo," Analytical Chemistry, 88(3): 1842-1849 (2016).
Zhang et al., "Recent Advances in Near-Infrared Absorption Nanomaterials as Photoacoustic Contrast Agents for Biomedical Imaging," Chinese Journal of Chemistry, 33(1): 35-52 (2014).
Ischenko, "Structure and Spectral-Luminescent Properties of Ploymethine Dyes," Russian Chemical Reviews, 60(8):865-880 (1991).
Viniychuk et al., "Electronic Transitions in Polymethine Dyes Involving Local and Delocalized Levels," Journal of Molecular Structure. 1060:30-37 (2013).
Cosco et al., "Flavylium Polymethine Fluorophores for Near- and Shortwave Infrared Imaging," Angewandte Chemie—International Edition, 56(42):13126-13129 (2009).
Gorka et al., "A near-IR uncaging strategy based on cyanine photochemistry," J Am Chem Soc., 136(40): 14153-14159 (2014).
Hong et al., "Multifunctional in Vivo Vascular Imaging Using Near-Infrared II Fluorescence," Nature Medicine, 18:1841-1846 (2012).
International Search Report and Written Opinion for International Application No. PCT/US18/25842 dated May 29, 2018.
International Search Report and Written Opinion for International Application No. PCT/US2018/036099 dated Aug. 26, 2018.
Nani et al., "Cyanine Photocages Enable the Near-IR Light Activation of Antibody-Drug Conjugates," Angew Chem Int Ed Engl., 54(46):13635-13638 (2015).

\* cited by examiner

HETEROCYCLYL POLYMETHINE IR CHROMOPHORES

REFERENCE TO RELATED APPLICATIONS

This application is the 371 U.S. National-Stage application of PCT/US2018/036099, filed Jun. 5, 2018, which claims the benefit of U.S. Provisional Application No. 62/515,459, filed Jun. 5, 2017, the contents of each of which are fully incorporated by reference herein.

BACKGROUND

Photomedicine broadly refers to the use of light for diagnostic or therapeutic procedures, including optical imaging, photothermal therapy (thermal ablation of cells) and photodynamic therapy (reactive oxygen species induced apoptosis or necrosis). (See Hamblin, M. R.; Huang, Y. Y. Handbook of Photomedicine; CRC Press: Boca Raton, 2014.) The low toxicity of light coupled with the direct control of localization and dosage make phototherapy a promising avenue for increasing the therapeutic index of disease treatment. (See Yuan, A.; Wu, J.; Tang, X.; Zhao, L.; Xu, F.; Hu, Y. J. Pharm. Sci. 2013, 102, 6-28.) Additionally, the inexpensive nature of lasers and detectors poise photo-imaging platforms as cost-effective preventative healthcare screening procedures. (See Massoud, T. F.; Gambhir, S. S. Genes Dev. 2003, 17, 545-580.) Despite its potential, photomedicine has encountered a key limitation: the penetration of light into tissue, defined as the point in which ⅔ of the light has been scattered or absorbed by endogenous biomolecules. (Tong, R.; Kohane, D. S. WIREs Nanomed. Nanobiotechnol. 2012, 4, 638-662.) As one moves toward lower energy light, the distance light can traverse through tissue increases. (See Weissleder, R. Nat. Biotechnol. 2001, 19, 316.) This is a well-known phenomenon that has resulted in a large push toward near-infrared (NIR, 700-1000 nm, FIG. 1) chromophores, fluorophores, and activatable probes. (Yuan, A.; Wu, J.; Tang, X.; Zhao, L.; Xu, F.; Hu, Y. J. Pharm. Sci. 2013, 102, 6.) However, short-wave infrared (SWIR, 1000-2000 nm, also referred to as the MR-II region) probes have not received as much attention, despite the fact that tissue penetration is superior in this region, especially when there is high blood content (FIG. 1). (Lim, Y. T.; Kim, S.; Nakayama, A.; Stott, N. E.; Bawendi, M. G.; Frangioni, J. V. Mol. Imaging 2003, 2, 50.)

Recently, Hongjie Dai and coworkers demonstrated using a carbon nanotube (CNT)-NIR-cyanine dye conjugate that the depth and resolution of in vivo imaging is superior above 1000 nm. (Hong, G.; Lee, J. C.; Robinson, J. T.; Raaz, U.; Xie, L.; Huang, N. F.; Cooke, J. P.; Dai, H. Nat. Med. 2012, 18, 1841.) The main limitation was the need for CNTs as a SWIR contrast agent, as there are concerns regarding the biocompatibility of CNTs. (Foldvari, M.; Bagonluri, M. Nanomedicine: Nanotechnol. Biol. Med. 2008, 4, 183.) While the potential of the SWIR has been demonstrated, materials that emit in this region are limited. Most reports of imaging in the SWIR have employed carbon nanotubes or quantum dots. Rare earth nanomaterials, as well as layer-by-layer assembled nanoparticles containing an organic dye have also been employed. However, all these materials are sizeable and do not represent a direct comparison to the fluorophores that have been enormously successful in vitro. What is necessary is the development of bright, stable, non-toxic small-molecule fluorophores that span the SWIR region and will allow for multiplexed imaging experiments. (See Antaris, A. L.; Chen, H.; Cheng, K.; Sun, Y.; Hong, G.; Qu, C.; Diao, S.; Deng, Z.; Hu, X.; Zhang, B.; Zhang, X.; Yaghi, O. K.; Alamparambil, Z. R.; Hong, X.; Cheng, Z.; Dai, H. Nat. Mater. 2015, 15, 235.)

SUMMARY OF THE INVENTION

Currently, there are only a handful of organic fluorophores that absorb and emit above 1000 nm, allowing excitation in the SWIR. Known SWIR-excitable fluorophores either have low or negligible quantum yields, or are too hydrophobic to be used directly for in vivo imaging.

The present disclosure provides SWIR-active small molecules with improved properties for use in optical imaging, photothermal therapy, photodynamic therapy, and SWIR-light promoted drug delivery. Accordingly, the present disclosure provides compounds of formula I:

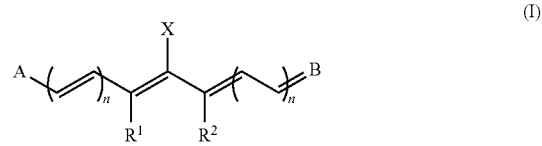

(I)

wherein:
A and B are independently selected from a bicyclic, tricyclic, or tetracyclic heterocyclyl or heteroaryl;
each instance of n is 0 or 1;
X is H, halo or is —N($R^3$)—$R^4$—N($R^5$)—C(O)O—Y;
$R^1$ and $R^2$ are independently selected from H or alkyl; or $R^1$ and $R^2$ together complete a cycloalkenyl ring;
$R^3$, $R^4$, and $R^5$ are independently selected from alkyl; and
Y is a cargo moiety.

The present disclosure also provides methods of using these dyes for in vivo sensing or cargo delivery, and methods of preparing these dyes.

DETAILED DESCRIPTION OF THE INVENTION

Figure 1:
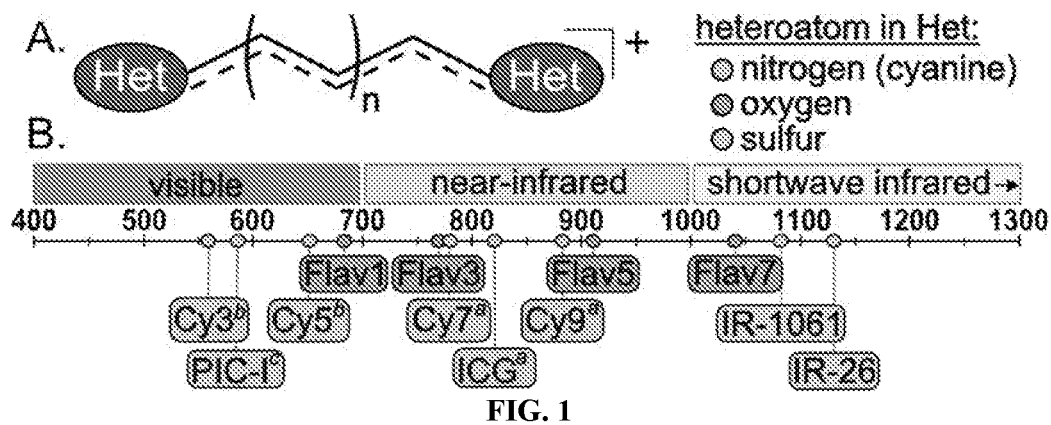
FIG. 1A shows a generalized polymethine dye scaffold.
FIG. 1B shows the $\lambda_{max,em}$ for selected polymethine dyes.

In certain aspects, the present disclosure provides compounds of formula I:

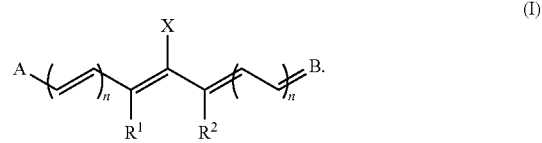

(I)

In formula I:

A and B are independently selected from a bicyclic, tricyclic, or tetracyclic heteroaryl;

each instance of n is 0 or 1;

X is H, halo or is —Z—$R^4$—N($R^5$)—C(O)O—Y;

Z is N($R^3$) or S;

$R^1$ and $R^2$ are independently selected from H or alkyl; or $R^1$ and $R^2$ together complete a cycloalkenyl ring, a heterocyclyl ring, or a polycyclyl ring system;

$R^3$, $R^4$, and $R^5$ are independently selected from alkyl; and

Y is a cargo moiety.

In certain embodiments of the compound of formula (I), at least one of A and B is not:

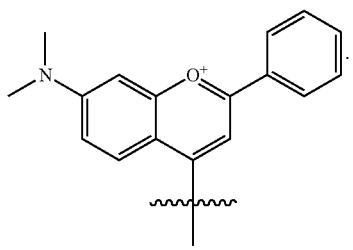 [SMILES: *c1cc(-c2ccccc2)[o+]c2cc(N(C)C)ccc12]

In certain embodiments of the compound of formula (I), $R^1$ and $R^2$ are independently selected from H or alkyl. In other embodiments, $R^1$ and $R^2$ together complete a cycloalkenyl ring.

In certain embodiments of the compound of formula (I), the compound is a compound of formula II:

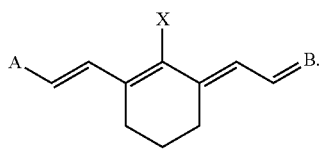

(II)

In certain embodiments of the compound of formula (I), A and B are the same. In other embodiment, A and B are different.

In certain embodiments of the compound of formula (I):

A is optionally substituted by one or more substituents independently selected from $R^7$;

B is optionally substituted by one or more substituents independently selected from $R^7$;

each instance of $R^6$ is independently selected from H, alkyl, such as fluoroalkyl or sulfonatoalkyl, acyl, cycloalkyl, heterocyclyl, aryl, or heteroaryl; or two instances of $R^6$ connected to the same N may complete a heterocyclyl; and each instance of $R^7$ is independently selected from alkyl (such as haloalkyl, fluoroalkyl or sulfonatoalkyl), alkoxy (such as haloalkyloxy, fluoroalkyloxy or sulfonatoalkyloxy), acyl, cycloalkyl, heterocyclyl, aryl, heteroaryl, N($R^6$)$R^6$, sulfonate, carbonate, cyano, ester, amide, or halo.

In certain embodiments of the compound of formula (I):

A is optionally substituted by one or more substituents independently selected from $R^7$;

B is optionally substituted by one or more substituents independently selected from $R^7$;

each instance of $R^6$ is independently selected from H, alkyl, such as fluoroalkyl or sulfonatoalkyl, acyl, cycloalkyl, heterocyclyl, aryl, or heteroaryl; or two instances of $R^6$ connected to the same N may complete a heterocyclyl; and each instance of $R^7$ is independently selected from alkyl, such as fluoroalkyl or sulfonatoalkyl, acyl, cycloalkyl, heterocyclyl, aryl, heteroaryl, N($R^6$)$R^6$, sulfonate, or carbonate.

In certain embodiments of the compound of formula (I), at least one $R^7$ is a water-solubilizing group. In further embodiments, the water-solubilizing group is selected from carboxylate group, a sulfonate, an anionic-substituted alkyl, or an anionic-substituted alkyl ether In certain embodiments of the compound of formula (I), at least one $R^7$ is an electron-withdrawing group. In further embodiments, wherein the electron-withdrawing group is selected from haloalkyl, cyano, sulfonate, sulfonatoalkyl, sulfonatoalkyloxy, carboxyl, ester, amide, halo, nitro, alkylammonium, amine oxide, or haloalkyl such as trifluoromethyl. In certain embodiments of the compound of formula (I), at least one $R^7$ is an electron-donating group.

In certain embodiments of the compound of formula (I), at least one $R^7$ is selected from fluoroalkyl, for instance to render the compound soluble in a fluorous medium. In further embodiments, at least one $R^7$ is $(CH_2)_3C_6F_{13}$.

In certain embodiments of the compound of formula (I), A and B are independently selected from carbazolyl, phenanthrolinyl, dibenzofuranyl, acridinyl, phenanthridinyl, xanthenyl,

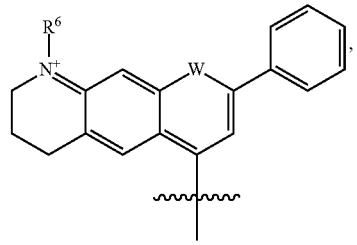

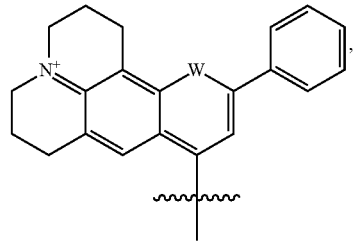

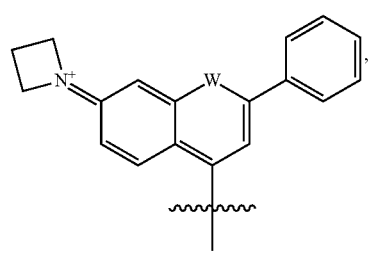

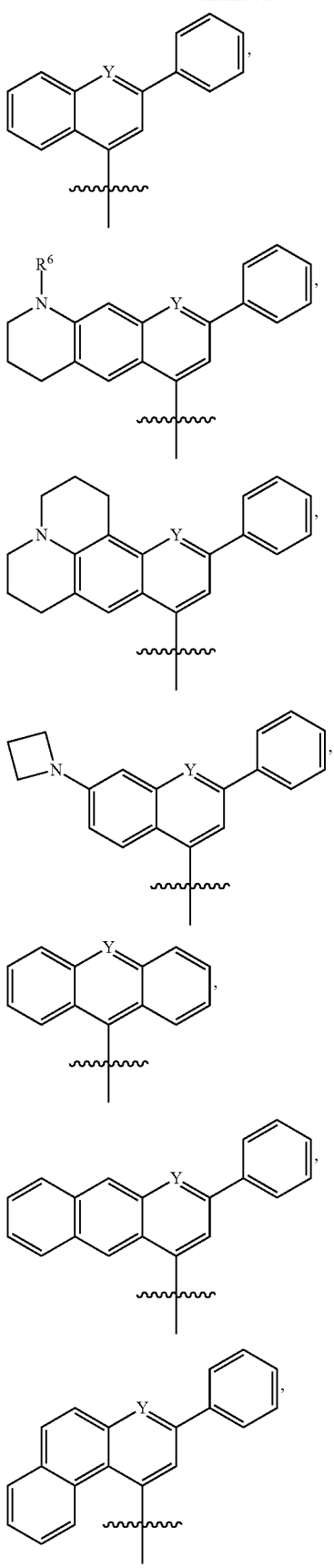
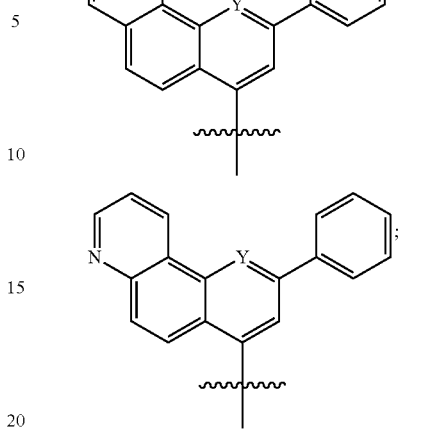
A and B are independently optionally substituted with one or more $R^7$, up to the limits of valence; and
W is SO, $SO_2$, $PR^6$, $PO_2H$, $POR^6$, SeO, $SeO_2$, TeO, $TeO_2$, $SiR^6{}_2$, $GeR^6{}_2$, BH, BOH, or $BR^6$; and
Y is $O^+$, $S^+$, $Se^+$, $Te^+$, SiR, $GeR^6$, N, $NR^{6+}$, or NO.
In certain embodiments of the compound of formula (I), A and B are independently selected from
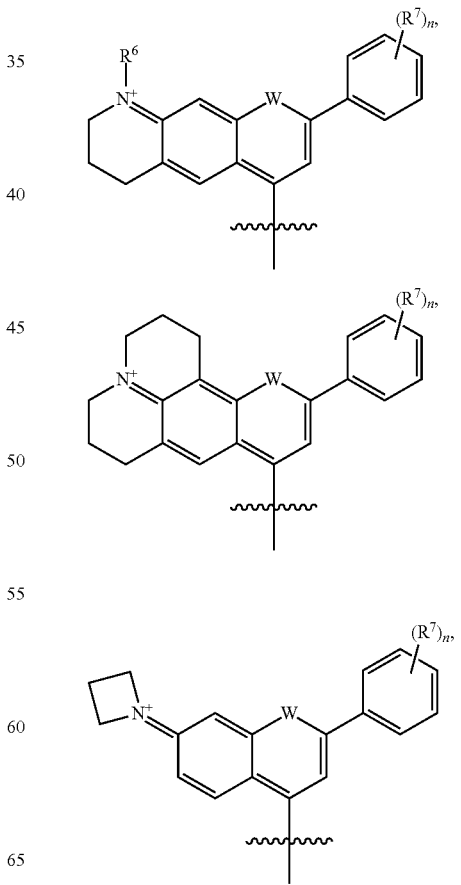

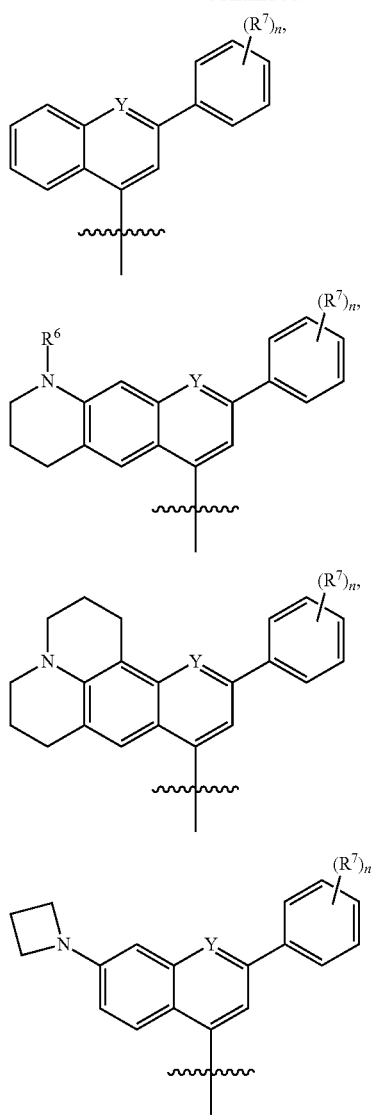
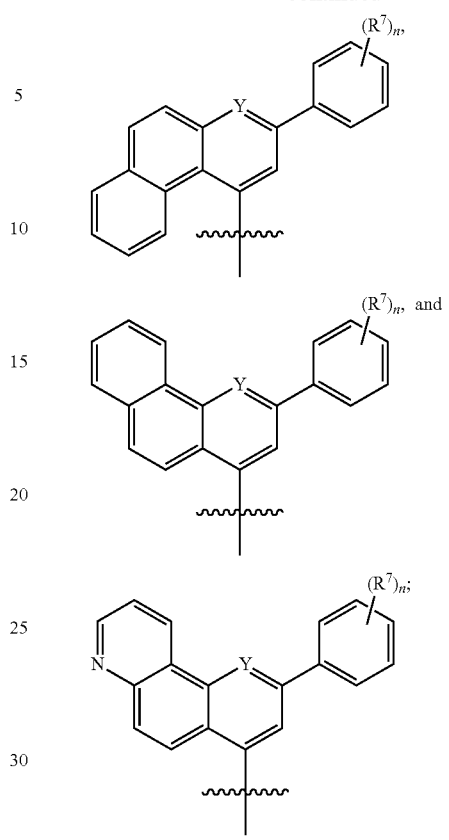
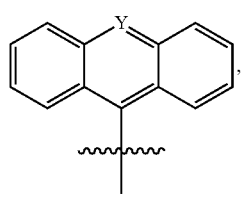
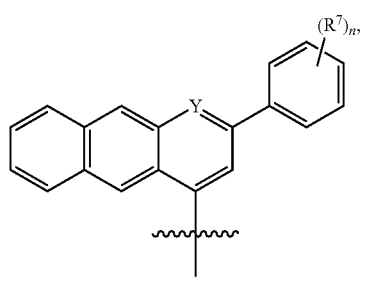
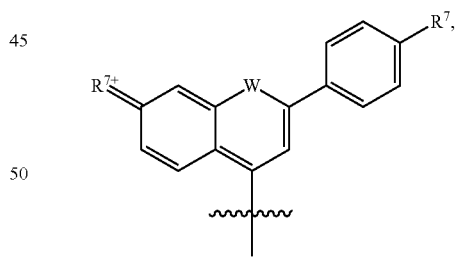
and n is 0, 1, 2, 3, 4, or 5, preferably 0 or 1. In certain such embodiments, wherein m is 0. In certain embodiments, n is 0. In certain embodiments, n is 1. In certain such embodiments, the $R^7$ on the phenyl is at the para position.
In certain embodiments of the compound of formula (I), A and B are independently selected from
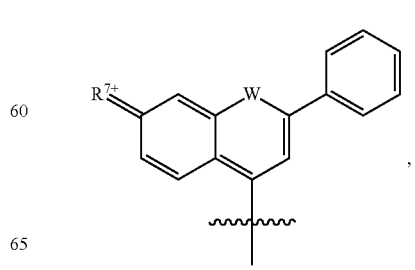

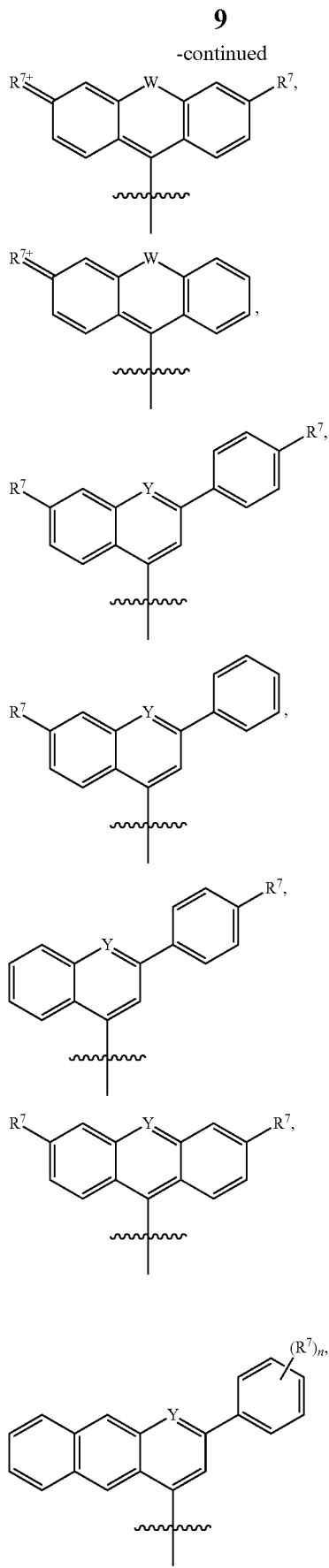
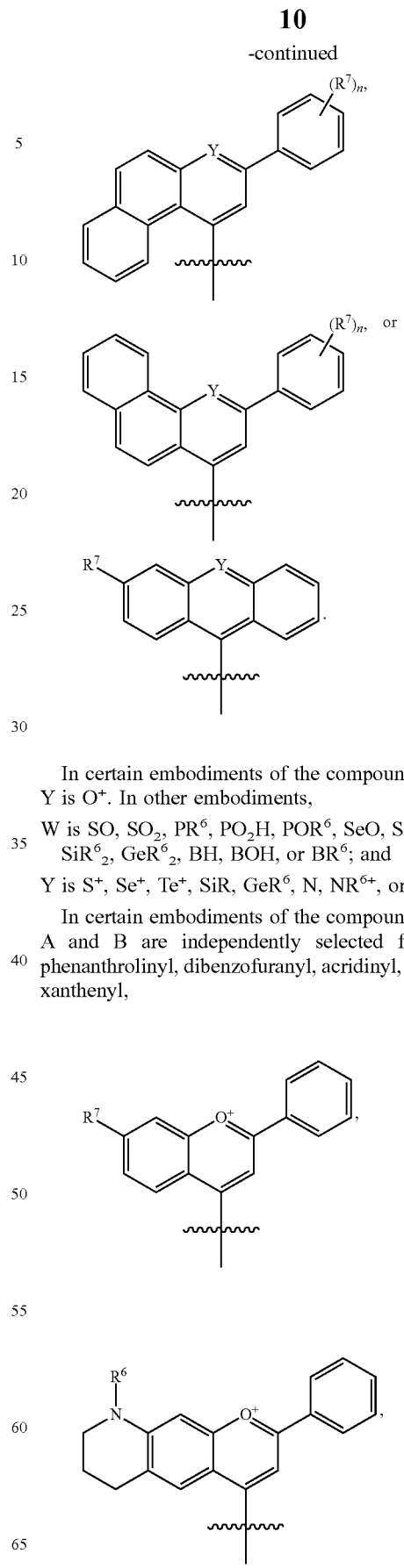

In certain embodiments of the compound of formula (I), Y is O+. In other embodiments, W is SO, SO$_2$, PR$^6$, PO$_2$H, POR$^6$, SeO, SeO$_2$, TeO, TeO$_2$, SiR$^6_2$, GeR$^6_2$, BH, BOH, or BR$^6$; and Y is S+, Se+, Te+, SiR, GeR$^6$, N, NR$^{6+}$, or NO.

In certain embodiments of the compound of formula (I), A and B are independently selected from carbazolyl, phenanthrolinyl, dibenzofuranyl, acridinyl, phenanthridinyl, xanthenyl, -continued

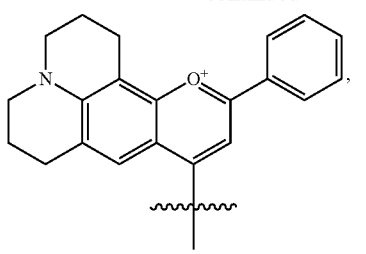

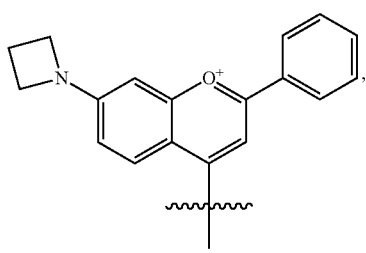 [SMILES: *c1cc(-c2ccccc2)[o+]c2cc(N3CCC3)ccc12]

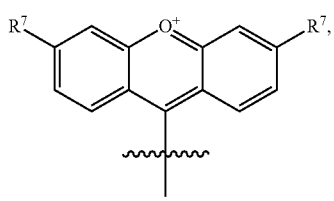

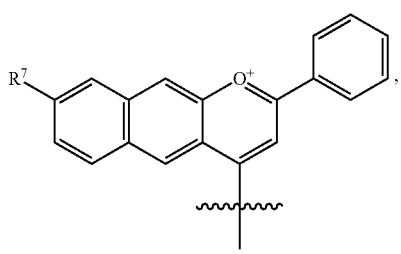

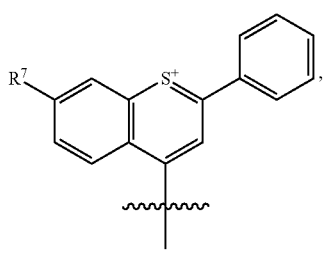

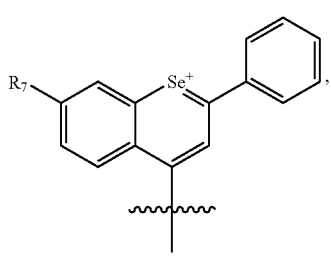

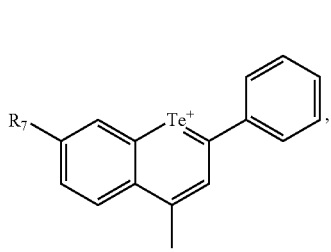

-continued

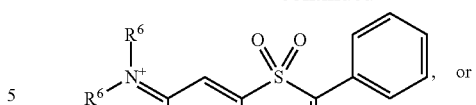

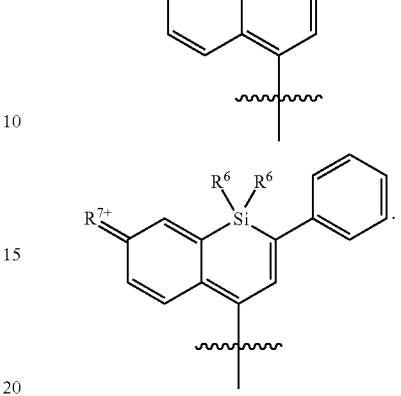

In certain embodiments of the compound of formula (I), X is halo. In other embodiments, X is Z—R$^4$—N(R$^5$)—C(O)O—Y.

In certain embodiments of the compound of formula (I), at least one of A and B is a tricyclic or tetracyclic moiety.

In certain embodiments of the compound of formula (I), at least one of A and B is a tricyclic moiety, e.g. at least one of A and B is carbazolyl, phenanthrolinyl, dibenzofuranyl, acridinyl, phenanthridinyl, xanthenyl,

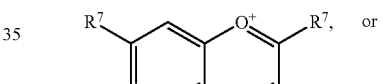

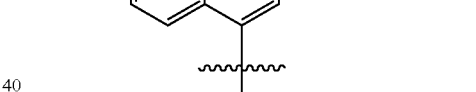

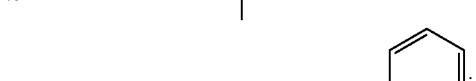

In certain embodiments of the compound of formula (I), at least one of A and B is a tetracyclic moiety, e.g. at least one of A and B is selected from

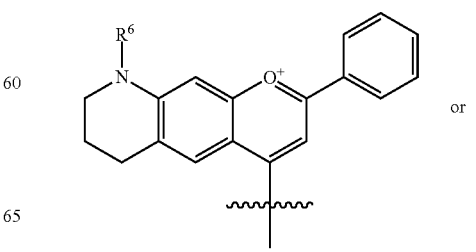

-continued

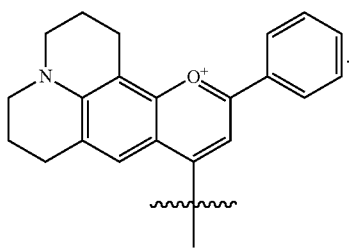

In certain embodiments of the compound of formula (I), at least one of A and B comprises a heteroatom other than nitrogen or oxygen. In certain embodiments, at least one of A or B comprises a heteroatom selected from sulfur, silicon, or selenium.

In certain embodiments of the compound of formula (I), at least one of A and B is selected from:

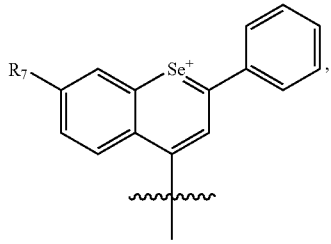

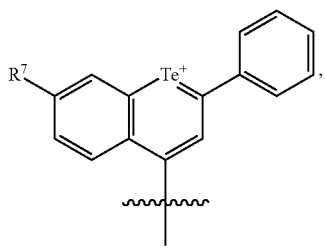

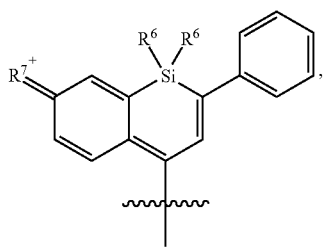

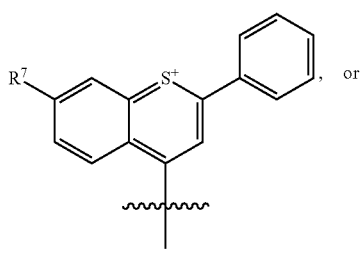, or

-continued

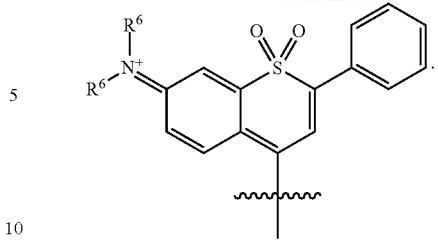

In certain embodiments of the compound of formula (I), at least one of A and B is substituted with $N(R^8)R^9$, wherein $R^8$ is cycloalkyl, heterocyclyl, aryl, or heteroaryl, and $R^9$ is selected from H, alkyl, acyl, cycloalkyl, heterocyclyl, aryl, or heteroaryl; or wherein $R^8$ and $R^9$ together complete a heterocyclyl. In certain embodiments, at least one of A and B is substituted with a 4-8 member N-linked heteroaryl or heterocyclyl. In certain embodiments, at least one of A and B is

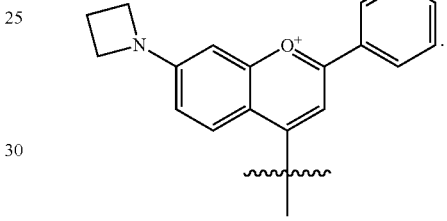

In certain embodiments of the compound of formula (I), at least one of A and B is substituted with sulfate, sulfonate, such as sulfonatoalkyl, or carboxylate. In certain embodiments, at least one of A and B is substituted with a fluoroalkyl.

In certain embodiments of the compound of formula (I), one or both of A and B is ionic such that the compound of formula (I) as a whole bears a charge. Such compounds may be paired with any suitable counter ion of interest, for example $BF_4^-$, tetraarylborate, $Cl^-$, $Br^-$, $I^-$, $ClO_4^-$, $OAc^-$, trifluoroacetate, arylacetate, sulfonate, or phosphate.

In certain aspects, the present disclosure provides pharmaceutical compositions comprising a compound as described herein.

In certain aspects, the present disclosure provides methods of delivering a compound or composition disclosed herein to a living animal, comprising administering the compound or composition to the living animal.

In certain aspects, the present disclosure provides methods of obtaining an image comprising illuminating a compound disclosed herein with excitation light, thereby causing the compound to emit fluorescence; and detecting the fluorescence. In certain embodiments, the image is obtained in vivo. In certain embodiments, the methods further comprise administering the compound to a living animal.

In certain aspects, the present disclosure provides methods of administering a therapy comprising administering a compound or composition disclosed herein, for example to an animal. In certain embodiments the methods further comprise illuminating the compound with excitation light. In certain embodiments, the methods further comprise generating singlet oxygen by illuminating the compound with excitation light. In certain embodiments, in the compound of formula (I), X is Z—R⁴—N(R⁵)—C(O)O—Y; and the methods comprise releasing the cargo moiety by illuminating the compound with excitation light.

In certain aspects, the present disclosure provides methods of preparing a compound as disclosed herein, comprising:

providing a starting material compound of formula I wherein A and B are the same:

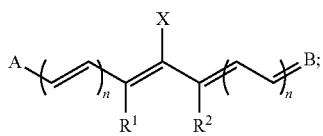

contacting the starting material compound with a basic amine, such as imidazole, dimethylamino pyridine, aniline, carbazole, or 1,8-diazabicyclo[5.4.0]undec-7-ene, thereby producing a half-dye intermediate;

providing a compound of formula (IV):

R⁸-D   (IV); and contacting the half-dye intermediate with the compound of formula (IV), thereby producing the compound;

wherein:

A, B, and D are heteroaryl selected as described above and elsewhere herein for instance they are selected from a bicyclic, tricyclic, or tetracyclic heteroaryl;

A and D are different.

each instance of n is 0 or 1;

X is H, halo or is —Z—R⁴—N(R⁵)—C(O)O—Y;

Z is N(R³) or S;

R¹ and R² are independently selected from H or alkyl; or R¹ and R² together complete a cycloalkenyl ring, a heterocyclyl ring, or a polycyclyl ring system;

R³, R⁴, and R⁵ are independently selected from alkyl;

R⁸ is alkyl, such as methyl; and

Y is a cargo moiety.

Small Molecule SWIR Chromophores

To obtain a SWIR small molecule chromophore, a narrow gap between the highest occupied molecular orbital (HOMO) and lowest unoccupied molecular orbital (LUMO) must be achieved. As the HOMO-LUMO gap of chromophores decreases, their reactivity increases. Thus, stability of SWIR chromophores is a more significant challenge than for MR chromophores. Another consequence of the small energy difference between the ground state and excited state is that there are many non-emissive pathways which can facilitate relaxation back to the ground state, resulting in low quantum yields of fluorescence ($\Phi_F$). Finally, for SWIR photodynamic therapy applications, the triplet energies of the photosensitizer need to be high enough to sensitize oxygen (23 kcal/mol).

Currently, there are only a handful of organic fluorophores that absorb and emit above 1000 nm, allowing excitation in the SWIR. Known SWIR-excitable fluorophores either have low or negligible quantum yields, or are too hydrophobic to be used directly in in vivo imaging.

The present disclosure provides SWIR-active small molecules with improved properties for use in optical imaging, photothermal therapy, photodynamic therapy, and SWIR-promoted drug delivery.

Dimethylamino Flavylium Dyes

While cyanines have been the premier polymethine dyes for applications in the visible and NIR, their extension into the SWIR has been limited. Lengthening the polymethine chain, which is known to impart a bathochromic shift to cyanine dyes, can compromise the fluorescence quantum yield ($\Phi_F$), decrease fluorophore stability, and lead to loss of electron delocalization over the entire conjugated system. Heterocycle modification can create bright, stable polymethine dyes in the SWIR. However, the photophysical changes that result from heterocyclyl modification are not straightforward. Extending heterocycle conjugation or adding electron-donating groups have been shown to bathochromically-shift polymethine dyes. Alternately, varying the heteroatom from oxygen down the chalcogens results in red-shifted absorption of ~30-100 nm for each step, although the emission is compromised by increased intersystem crossing due to spin-orbit coupling. Dimethylamino flavylium polymethine dyes have been prepared and analyzed.

Scheme 1.
Synthesis of dimethylamino flavylium polymethine dyes 3-6.

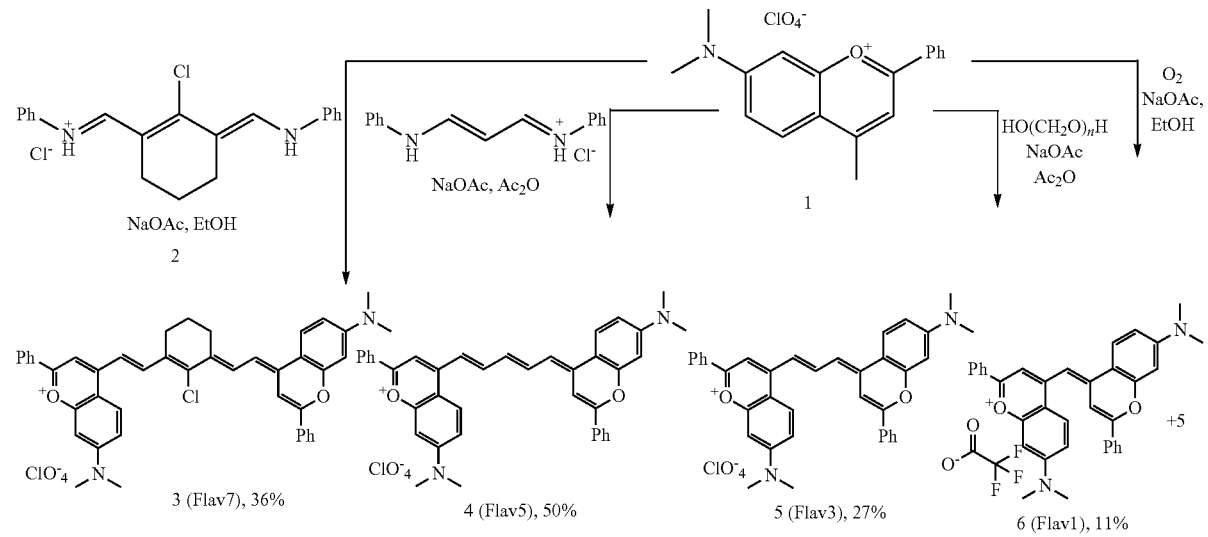

Polymethine dyes can be prepared through the introduction of an activated heterocycle to an aldehyde or bis-aldehyde equivalent. The requisite 7-N,N-dimethylamino-4-methyl-flavylium heterocycle (1) was prepared in three steps from dimethylaminophenol as previously reported (Chen, J.-R.; Wong, J.-B.; Kuo, P.-Y.; Yang, D.-Y. Org. Lett. 2008, 10, 4823-4826):

Scheme 2:
Preparation of 7-N,N-dimethylamino-4methyl-flavylium heterocycle (1)

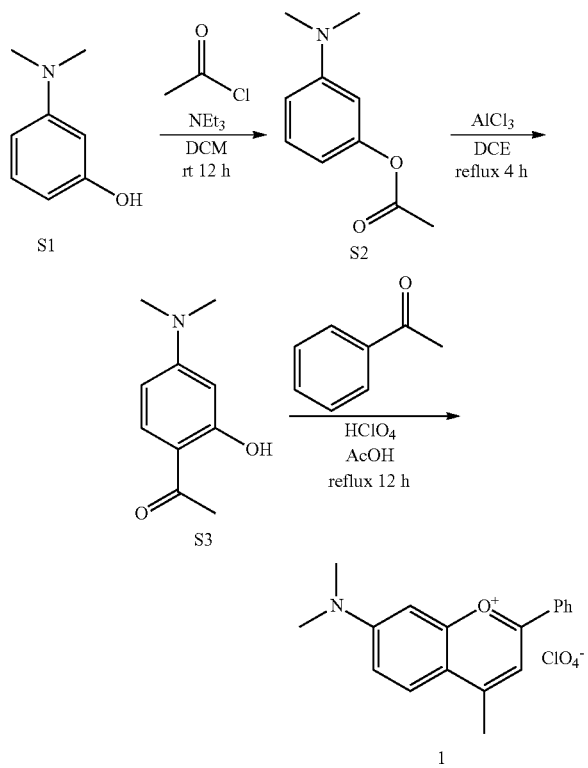

Combining 1 with N-[(3-(anilinomethylene)-2-chloro-1-cyclohexen-1-yl)methylene] aniline 2, malonaldehyde bis(phenylimine), and paraformaldehyde under basic conditions yielded dimethylamino flavylium dyes 3, (Flav7), 4 (Flav5), and 5 (Flav3), respectively. The formation of 3 proceeded in anhydrous ethanol with sodium acetate and 2. Under these conditions, a mixture of highly colored products was obtained which included Flav7 and surprisingly 5 (Flav3) and 6 (Flav1). Treatment of 1 with base in ethanol, without an electrophile, allowed access to a mixture of 6 and 5. This was determined to be an oxygen dependent transformation. It is hypothesized that the oxygen undergoes radical addition to the flavylium to generate a peroxyflavylium which combines with deprotonated 1 to yield Flav1 and an equivalent of formaldehyde. The Flav3 can then be formed via the combination of formaldehyde and 1. The syntheses of 4-5 were optimized to proceed in deoxygenated acetic anhydride. The perchlorate counterions in 3-5 were confirmed by X-ray photoelectron spectroscopy.

Figure 2:
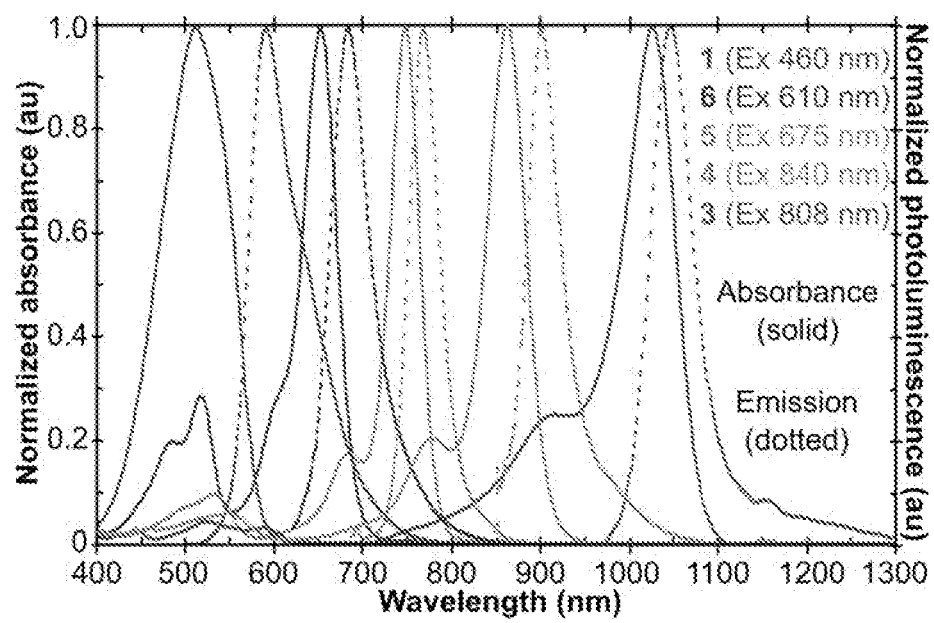
FIG. 2 shows the normalized absorbance (solid) and photoluminescence (dotted) of 5, 7-10 in dichloromethane.

The absorption, emission, and photostability properties of flavylium dyes 3-6 were measured. As seen in FIG. 2 and Table 1, the flavylium dyes span the long wavelength end of the visible, the NIR and enter the SWIR.

TABLE 1

Photophysical characterization of 1, 3-6.

| | absorption (DCM) | | emission (DCM) | | |
|---|---|---|---|---|---|
| | $\lambda_{max}$ (nm) | $\varepsilon$ $(M^{-1}cm^{-1})^a$ | $\lambda_{max}$ (nm) | $\Phi_F{}^a$ | QE, $\varepsilon\Phi_F$ $(M^{-1}cm^{-1})$ |
| 1 | 510 | 17000 | 587 | — | — |
| 6 | 650 | 16000 | 684 | 0.7% | 100 |
| 5 | 746 | 220000 | 766 | 2.9% | 6600 |
| 4 | 862 | 240000 | 908 | 5% | 10000 |
| 3 | 1026 | 236000 | 1045 | 0.53% | 1200 |

The dimethylamino flavylium dyes are significantly red-shifted from classic cyanine dyes by approximately 200 nm and Flav7 absorbs ~40 nm past IR-27. Photostabilities of the Flav series were measured under continuous-wave irradiation (532 nm, 0.53 fluence). Flav1, Flav3 and Flav5 all show excellent photostabilities in dichloromethane, with Flav7 displaying reasonable stability (Table 2).

TABLE 2

Photobleaching rates of 3-6.

| | raw rate, k $(s^{-1} \times 10^{-3})$ | $\varepsilon$ at 532 nm $(M^{-1}cm^{-1} \times 10^4)$ | relative rate, $k_{rel}$ $(s^{-1} \times 10^{-3})$ |
|---|---|---|---|
| 6 | 0.43 ± 0.01 | 0.23 ± 0.08 | 4 ± 1 |
| 5 | 1.00 ± 0.06 | 2.0 ± 0.1 | 1.00 ± .06 |
| 4 | 2.6 ± 0.2 | 1.29 ± 0.08 | 4.0 ± 0.2 |
| 3 | 28. ± 3. | 1.4 ± 0.2 | 40. ± 6. |

The Flav1 dye absorbs at 650 nm, similar to a 5-cyanine, but has a lower absorption coefficient (ε) and $\Phi_F$, resulting in a low quantum efficiency (QE, defined as $\varepsilon\Phi_F$), consistent with the short polymethine chain. The Flav3 dye has similar absorption properties to the standard heptamethine indocyanine dye 1,1',3,3,3',3'-hexamethylindotricarbocyanine iodide (HITCI, Cy7) with $\lambda_{max,abs}$~745 nm and ε~220,000 $M^{-1}$ $cm^{-1}$. While HITCI has ~10-fold higher $\Phi_F$ than Flav3 Flav3 is 4-fold more photostable. The Flav5 and Flav7 dyes are more red-shifted than indoline-containing cyanine dyes, absorbing at 862 nm and 1026 nm, respectively. The Flav5 emits at 908 nm, a relatively unique wavelength for polymethine dyes, with extremely high QE ($10^3$ $M^{-1}$ $cm^{-1}$), desirable photostability, and the largest Stoke's shift of the series at 46 nm. Finally, the Flav7 is a true NIR-II/SWIR fluorophore with emission at 1061 nm, $\Phi_F$ of 0.53%, and an impressive SWIR QE of 1,200 $M^{-1}$ $cm^{-1}$.

This family of flavylium dyes has photophysical qualities that are complementary to commonly used cyanine dyes. However, the premier dye in the series is the Flav7 (3) as few emissive polymethine dyes exist in this region. Thus, we thoroughly investigated its stability. First, we explored the solvatochromism of Flav7. The $\lambda_{max,abs}$ in dichloromethane, dimethyl sulfoxide, acetonitrile, tetrahydrofuran, acetone exhibited minimal variation. However, in polar solvents, spectral broadening and accentuation of a high-energy shoulder were observed. This behavior is consistent with SWIR polymethine dyes that experience ground state symmetry breaking due to stabilization of an asymmetric electronic structure. In methanol, an immediate color change is observed, suggestive of covalent modification of the polymethine; however, a major decomposition product could not be identified.

Concerned about the structure's susceptibility to nucleophilic attack, the stability of Flav7 in the presence of methanol, ethanol, and water was investigated. 3 was dissolved in acetonitrile, and 1-50% water, ethanol, or methanol was introduced. Changes in absorption spectra over time were monitored. Consistent with the solvatochromism study, even 1% methanol resulted in the rapid loss of $\lambda_{max,abs}$ at 1013 nm. In contrast, adding 10% ethanol or water resulted in slight loss and no significant change, respectively, over 4 hours, indicating that Flav7's reactivity with methanol is unique. Further evidence that 3 is stable to water include UV/Vis monitoring of the dose-dependent addition of water to 3 in acetonitrile followed by water removal. Upon water addition, a loss of $\lambda_{max,abs}$ at 1013 nm with concomitant appearance of a peak from 750-850 nm is observed (FIG. S9), but absorbance at 1013 nm is restored upon water removal (FIG. S10).

Monitoring a solution of 0.1 mg/mL 3 in acetonitrile with 10% water over time by LCMS showed no appreciable degradation. Collectively, these data suggest that Flav7 undergoes aggregation, not covalent modification, in water. Finally, the photoluminescence of Flav7 was compared to the prominent SWIR polymethine dyes, IR-26 and IR-1061. IR-26 has been widely-employed as a standard for this region, while IR-1061 has recently been the active component of nanomaterials for MR-II in vivo imaging. Despite numerous studies which rely on these dyes, the reported $\Phi_F$ for IR-26 have been inconsistent, and the $\Phi_F$ of IR-1061 has yet to be thoroughly characterized. Consequently, to establish that Flav7 is more emissive than existing SWIR polymethine dyes, each dye's emission was directly compared using a SWIR camera. We prepared solutions of 3, IR-26, and IR-1061 in dichloromethane with identical absorbance at 808 nm, excited with a diffuse 808 nm laser, and imaged their emission over 1000-1500 nm. The average intensity was quantified for each cuvette in the same position within the field of view and clearly indicates that Flav7 is the brightest of the three dyes. These data correlate well with absolute $\Phi_F$ determined using an integrating sphere.

These $\Phi_F$ measurements of IR-26 are consistent with recent reports and contrast the prior accepted value. We conclude that the $\Phi_F$ of IR-26, IR-1061, and Flav7 are 0.046±0.03% ($\lambda_{max}$=1129 nm), 0.32±0.04% ($\lambda_{max}$=1081 nm), and 0.53±0.3% ($\lambda_{max}$=1045 nm), respectively. These data suggest that Flav7 or commercially available IR-1061 are better comparative sources for SWIR measurements. Furthermore, we deem direct comparative imaging experiments as the most reliable method to evaluate the brightness of fluorophores in the SWIR.

The dimethylamino flavylium dyes are notably red-shifted compared to prevalent cyanine dyes, and expand the opportunities for imaging and detection in the MR and SWIR. Certain methods for fluorescence imaging of animals are described, for instance, in U.S. Pat. No. 7,383,076. Typically, the stability and emission of fluorophores decrease as their absorption moves to lower energies, highlighting the challenge of achieving stable, bright fluorophores, particularly in the SWIR. However, the three NIR polymethine dyes reported display excellent photostabilities with varying quantum yields. Heptamethine Flav7 is 13-times brighter than IR-26, the current SWIR benchmark. We determined that Flav7 is the superior SWIR fluorophore using a comparative imaging experiment and absolute $\Phi_F$. Concurrent to our work, benzobisthiadiazole-thiophene fluorophores with shielding units have been developed for MR-II imaging. While this scaffold affords impressive $\Phi_F$, the high ε of polymethine dyes results in larger quantum efficiencies for our dimethylamino flavylium NIR/SWIR emitters. Polymethine fluorophores have other distinctive properties including narrow absorption and emission bands and the ability to be chemically fine-tuned, which poise them to be a promising fluorophore scaffold for new technologies in these underdeveloped regions of the EM spectrum. However, further improvements beyond these dimethylaminoflavylium dyes are still possible, and are described herein.

Modified Heterocyclic SWIR Dyes

The heterocycle composition of polymethine dyes has a significant effect on the photophysical properties of these chromophores. The present disclosure describes polymethine fluorophores that replace the flavylium heterocycle in the dyes described above with other heterocycles, including modified flavylium heterocycles. Alternatively, the dimethylaminoflavylium group may be extended to include other moieties that impart different physicochemical properties, or the amino may be replaced entirely with a more hydrophilic group. The modifications of the dimethylaminoflavylium group described herein are designed to enhance absorption coefficient (ε), fluorescence quantum yield ($\Phi_F$), the singlet oxygen quantum yield ($\Phi_\Delta$), and/or the absorption and emission wavelengths.

Minimizing degrees of freedom on fluorophores by extending the flavylium heterocycle reduces opportunities for internal conversion, in turn resulting in higher $\Phi_F$. Strategies to increase the $\Phi_F$ include rigidifying the dimethylamino flavylium, for instance as in the following heterocycles:

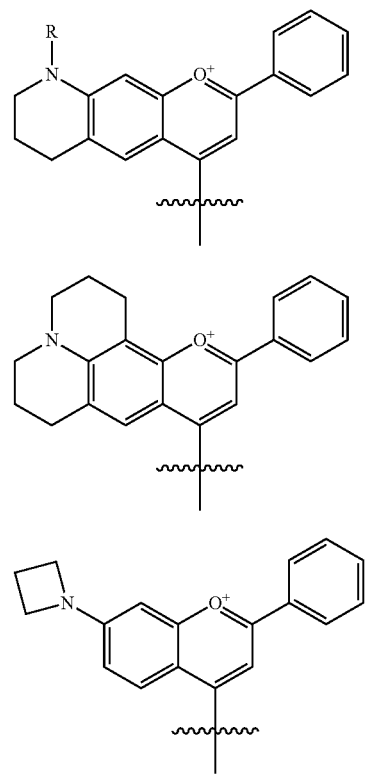

In these structures, R may represent alkyl, such as lower alkyl, cycloalkyl, such as lower cycloalkyl, aryl, or heteroaryl. In certain embodiments, R may represent alkyl, such as lower alkyl. Analogous substitutions may be made on the other modified heterocycles disclosed herein.

Those of skill in the art will appreciate that these heterocyclyl moieties, when conjugated to a polymethine, such as a pentamethine or a heptamethine, may be drawn in one of two or more resonance structures, depending on the end of the polymethine to which the moiety is attached as well as the other atoms in the heterocyclyl moieties. This is illustrated for 7 below:

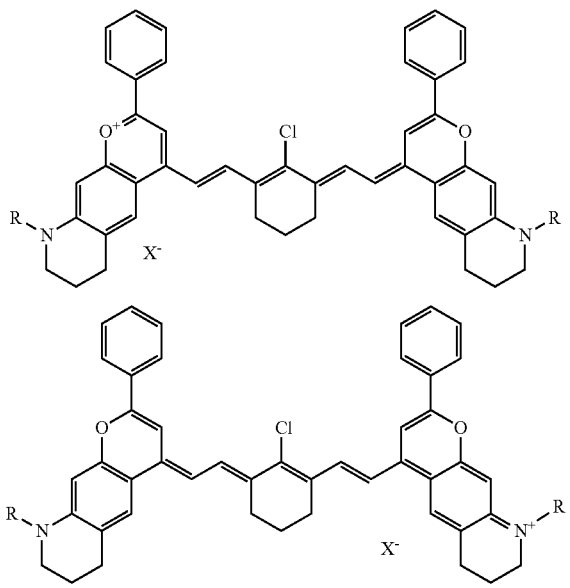

Throughout the present disclosure, when heterocyclyl moieties for conjugation to polymethines are drawn, all resonance structures are contemplated.

Extended aromatic systems may also be used to improve SWIR fluorophore properties, for instance, by resulting in a bathochromic shift. Exemplary heterocycles include carbazolyl, phenanthrolinyl, dibenzofuranyl, acridinyl, phenanthridinyl, xanthenyl, and the following:

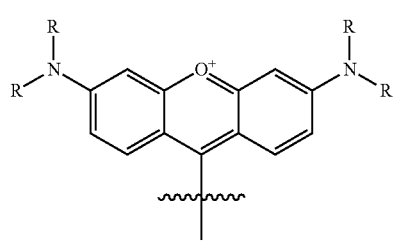

10

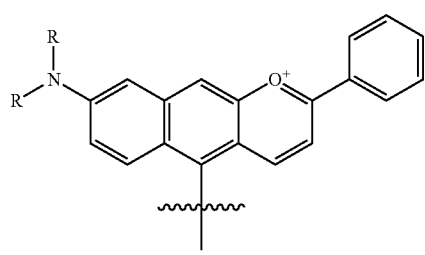

11A

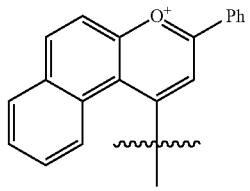

11B

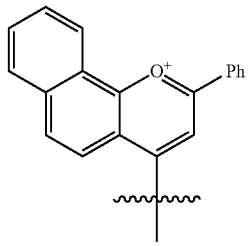

11C

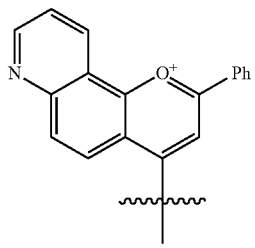

11D

In these structures, R may represent alkyl, such as lower alkyl, cycloalkyl, such as lower cycloalkyl, aryl, or heteroaryl. In certain embodiments, R may represent alkyl, such as lower alkyl. Analogous substitutions may be made on the other modified heterocycles disclosed herein.

Alternatively, or in addition, the flavylium oxygen (or the oxygen in the other heterocycles disclosed herein) may be replaced with another heteroatom, which may also be substituted as valence permits:

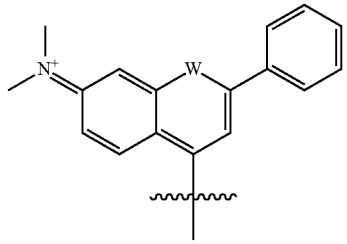

12A

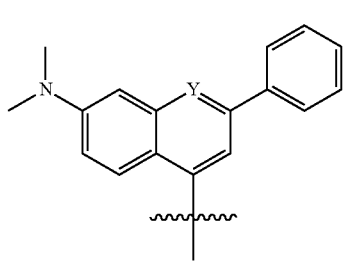

12B

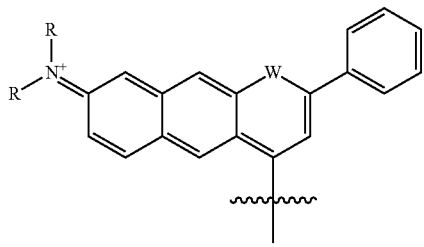

12C

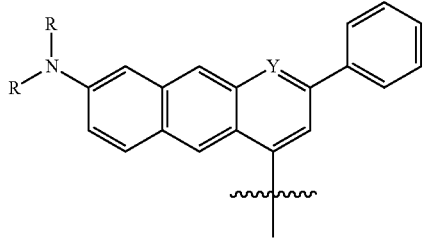

12D

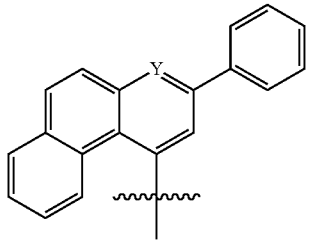

12E

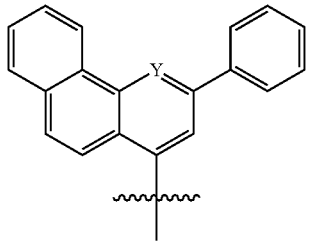

12F

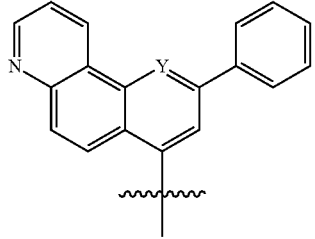

12G

In these structures, W may represent SO, SO$_2$, PR, PO$_2$H, POR, SeO, SeO$_2$, TeO, TeO$_2$, SiR$^6$$_2$, GeR$^6$$_2$, BH, BOH, or BR; Y may represent O$^+$, S$^+$, Se$^+$, Te$^+$, SiR, GeR, N, NR$^+$, or NO; and R may represent alkyl, such as lower alkyl, cycloalkyl, such as lower cycloalkyl, aryl, or heteroaryl. In certain embodiments, R may represent alkyl, such as lower alkyl. Analogous substitutions may be made on the other modified heterocycles disclosed herein.

For applications in photodynamic therapy the addition of heavy atoms, such as sulfur, promotes intersystem crossing through spin-orbit coupling. Exemplary heterocycles include:

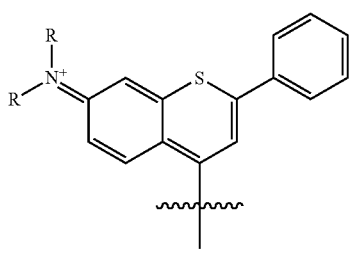

13

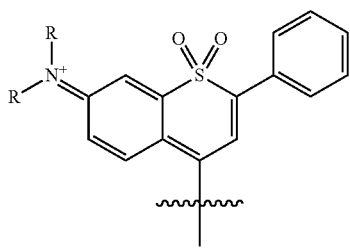

14

In these structures, R may represent alkyl, such as lower alkyl, cycloalkyl, such as lower cycloalkyl, aryl, or heteroaryl. In certain embodiments, R may represent alkyl, such as lower alkyl. Both tri-, penta- and heptamethine dyes containing these sulfur-containing heterocycles, as depending on the heterocycle used and on other properties of the dye, the addition of the sulfur can produce a red-shift such that the excited state of the heptamethine has an energy lower than that required for sensitization of oxygen. Polymethine dyes that readily cross to the triplet state, such as these may also be employed in oxygen sensitization.

Alongside achieving bright fluorophores in the SWIR, addressing photostability is a parallel goal. Again, photostability decreases with elongation of the methine chain such that even heptamethine dyes are often significantly less stable than their pentamethine counterparts. Adding electron withdrawing groups, such as sulfate, effectively deactivates the polymethine for reaction with electron poor species. Many electron withdrawing groups, including sulfate, also impart aqueous solubility. In the structures below, the electron-withdrawing group is indicated by R$^4$.

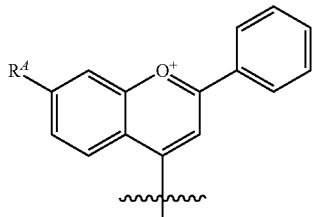

15

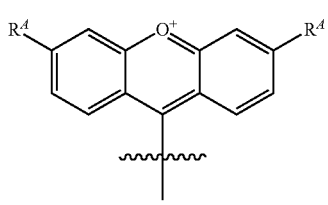

16

17

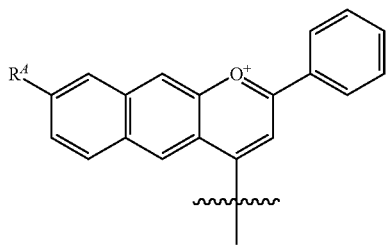

18

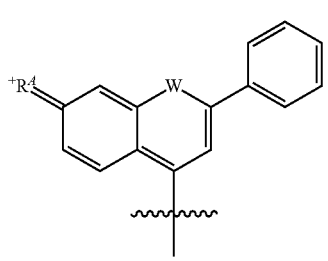

19

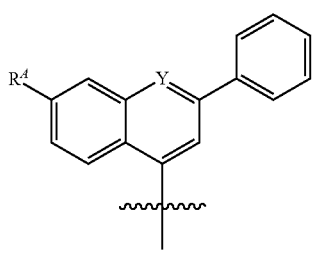

In these structures, W may represent SO, SO$_2$, PR, PO$_2$H, POR, SeO, SeO$_2$, TeO, TeO$_2$, SiR$^6_2$, GeR$^6_2$, BH, BOH, or BR; Y may represent O$^+$, S$^+$, Se$^+$, Te$^+$, SiR, GeR, N, NR$^+$, or NO; R may represent alkyl, such as lower alkyl, cycloalkyl, such as lower cycloalkyl, aryl, or heteroaryl; and R$^A$ may represent an electron-withdrawing group such as haloalkyl, cyano, sulfonate, sulfonatoalkyl, sulfonatoalkyloxy, carboxyl, ester, amide, halo, nitro, alkylammonium, amine oxide, or haloalkyl, such as trifluoromethyl. In certain embodiments, R$^A$ may represent sulfonate, sulfonatoalkyl, or sulfonatoalkyloxy, preferably sulfonate or a sulfonatoalkyl such as sulfonatoethyl. In certain embodiments, R$^A$ may represent an electron-donating group such as alkoxy, alkyl, or aryl. In certain embodiments, R may represent alkyl or lower alkyl. Analogous substitutions may be made on the other modified heterocycles disclosed herein.

Dimethylamino flavylium cyanine 3 is hydrophobic, which hinders its ability to be employed for in vivo imaging. Thus, the present disclosure provides variants that are hydrophilic and/or fluorophilic.

Hydrophilicity may be imparted to polymethine dyes by incorporating ionic groups such as sulfonates, as described above, or carboxylates. Carboxylates can also facilitate conjugation of biomolecules. Exemplary heterocycles include:

21A

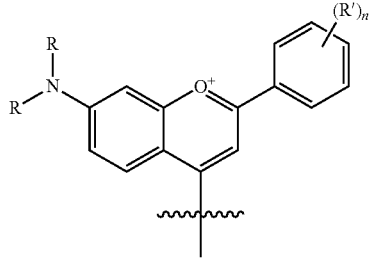

21B

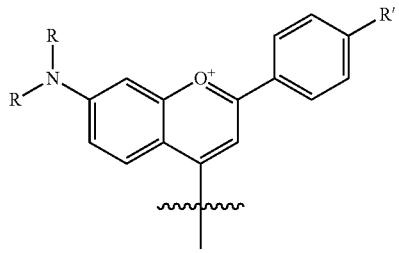

In the above structure, in addition to the values for R described above, any R group may independently be anionic-substituted alkyl, such as sulfonatoethyl. In some embodiments, R may be a nonionic alkyl and R' may be a carboxylate group, a sulfonate, an anionic-substituted alkyl, or an anionic substituted alkyl ether. R' may be located at any position on the aryl ring and one or more R' substituents may be present. Analogous substitutions may be made on the other modified heterocycles disclosed herein.

Fluorophilicity—i.e., the ability to enter the fluorous phase—may be imparted by incorporating a fluorinated alkyl chain into the dye, such as $(CH_2)_3C_6F_{13}$. Such fluorophilic dyes can be used to localize the dyes inside perfluorocarbon nanoemulsions. The fluorous phase, despite requiring a nanomaterial scaffold, has significant advantages for imaging in the SWIR, including the protection of cyanine dyes from biomolecules, increased quantum yields, and increased photostabilities. Exemplary heterocycles include:

22A

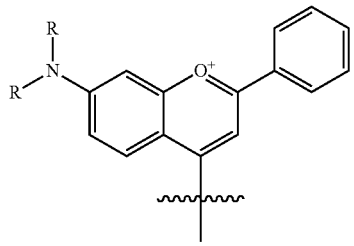

22B

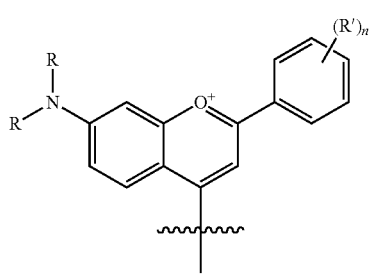

In the above structures, in addition to the values for R and R' described above, R may be a fluorinated alkyl, such as (CH$_2$)$_3$C$_6$F$_{13}$. In certain embodiments, R may be a fluorinated alkyl or fluorinated alkoxy, such as (CH$_2$)$_3$C$_6$F$_{13}$ or O(CH$_2$)$_3$C$_6$F$_{13}$. R' may be located at any position on the aryl ring and one or more R' substituents may be present. Analogous substitutions may be made on the other modified heterocycles disclosed herein.

It will be understood from the present disclosure that by appropriate selection or combination of substitutions on and within the heterocycles described herein, one or all of the properties described above may be achieved.

Exemplary Preparation of Modified Heterocyclic SWIR Fluorophores

Illustrative retrosynthetic analyses of heterocycles described herein are presented in Scheme A. Synthetic strategies for the heterocycles of the present disclosure are further described below, and the performance of exemplary syntheses is described in the Examples section.

Heterocycles 1, 7, and 8 may be produced according to a thermally promoted condensation between a 3-amino phenol derivative and ethyl benzoyl acetate, followed by Grignard addition of methyl magnesium bromide and treatment with HX to promote dehydration and install the counter ion (X) of interest. (Scheme 3A, route 1). Any suitable counter ion of interest may be used, for example BF$_4^-$, tetraarylborate, Cl$^-$, Br$^-$, I$^-$, ClO$_4^-$, OAc$^-$, trifluoroacetate, arylacetate, sulfonate, or phosphate. Other 7-amino flavylium heterocycle derivatives may be obtained from the commercial 7-hydroxyflavone which can undergo triflation with trifluoromethane sulfonic anhydride to produce a species reactive towards cross-coupling reactions. The 7-triflate flavone can then undergo Buchwald-Hartwig cross-coupling reactions with a variety of primary and secondary amines and amides (Scheme 3A, route 2) to produce the 7-amino functionalized flavone. This flavone is similarly reactive towards Grignard conditions to yield the functionalized flavylium heterocycle.

Scheme A
Retrosynthesis of Fluorophore Heterocycles

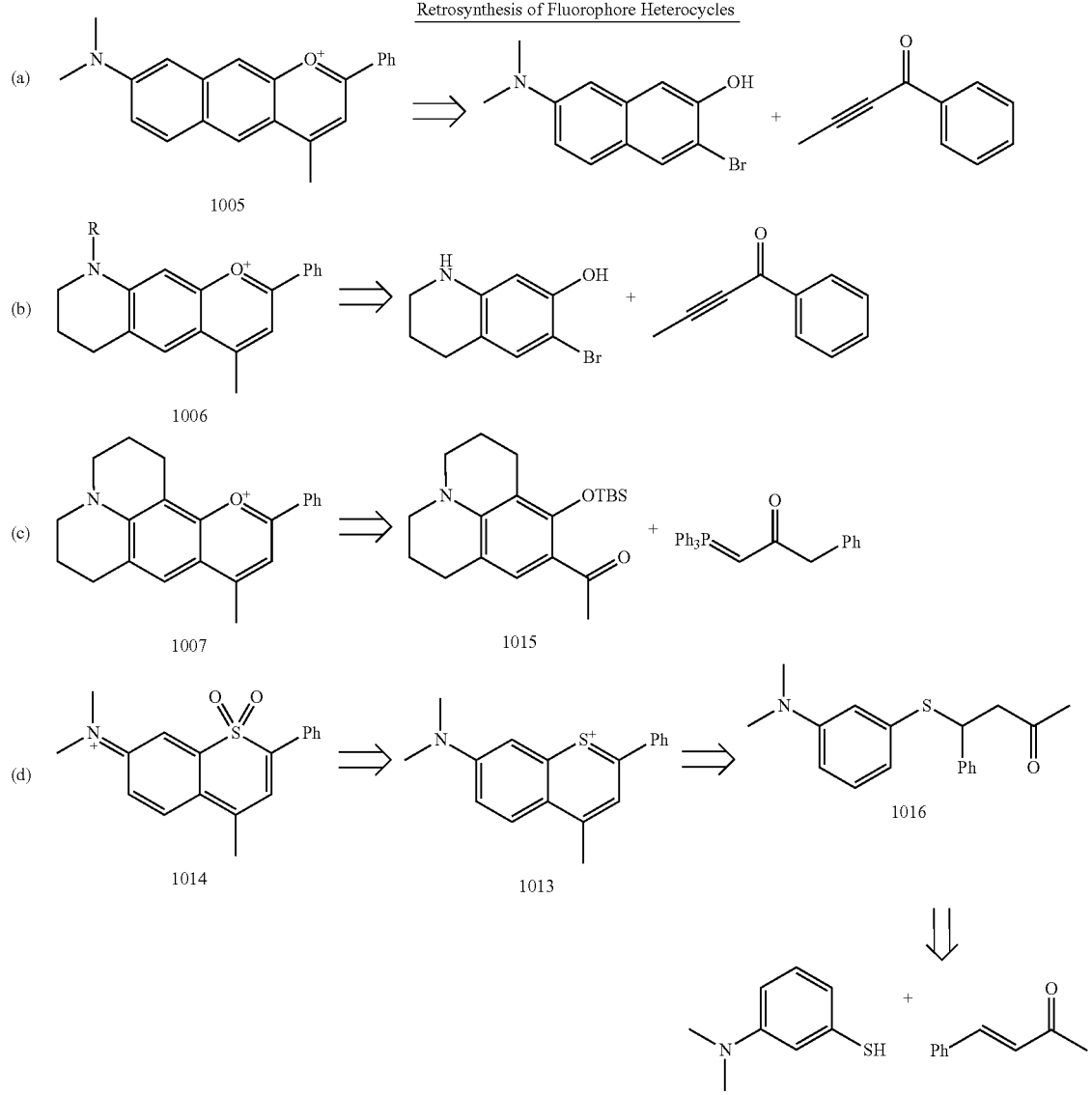

Finally, 7-amino functionalized derivatives may be obtained beginning with the commercial 7-amino flavone which can undergo nucleophilic addition reactions or reductive amination reactions to yield the functionalized flavone (Scheme 3A, route 3).

by the phenol oxygen into the pendant carbonyl, followed by dehydration. The route through a Michael reaction, exemplified in Scheme 3C may be achieved by lithiation of the ortho-bromophenol or brominated naphthalene precursors.

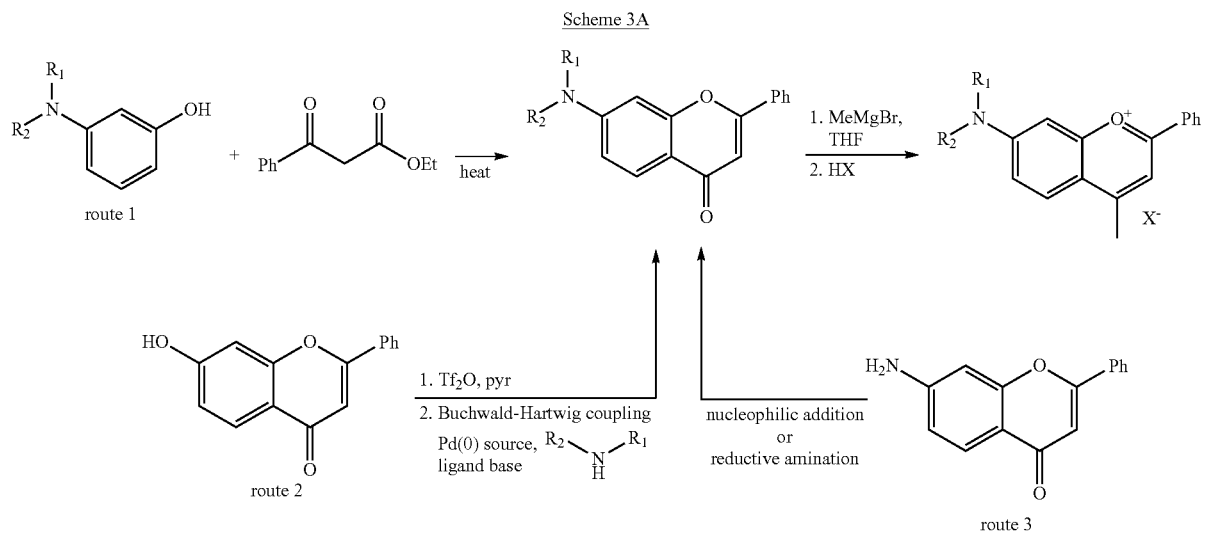

Heterocycles 11B, 11C, and 11D may be obtained by Grignard addition of methyl magnesium bromide to the corresponding flavones (Scheme 3B), which are either commercially available or can be obtained from previously reported routes (see, e.g., Foroozesh, M. J. Med. Chem. 2015, 58, 6481-6493.).

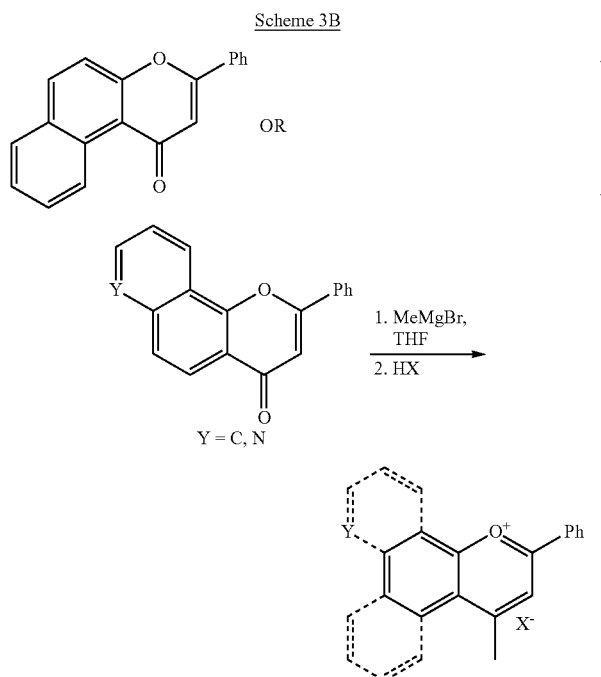

Heterocycle 11A may be produced by a 1,4-addition into butynophenone and subsequent internal nucleophilic attack

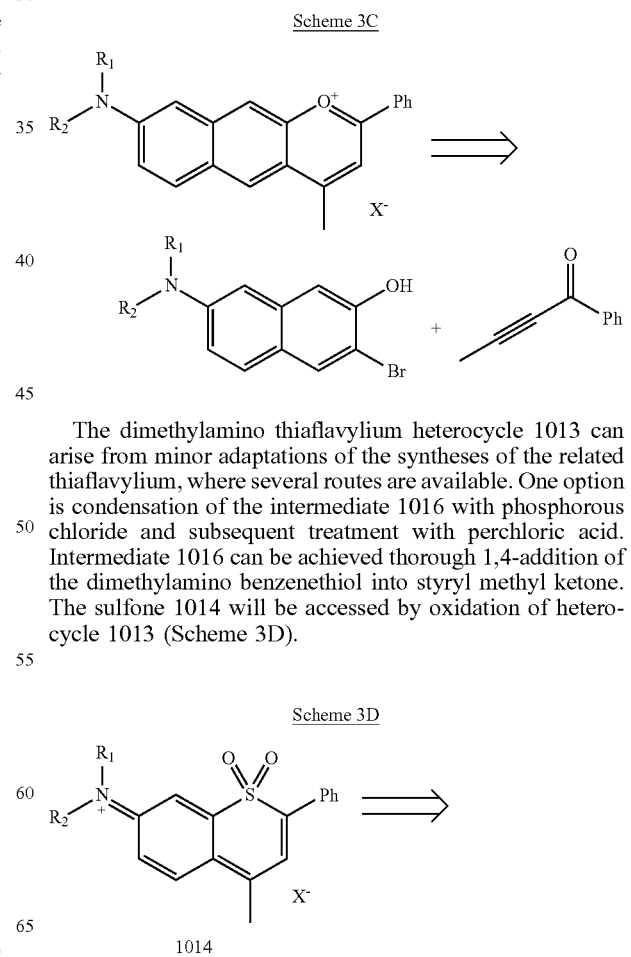

The dimethylamino thiaflavylium heterocycle 1013 can arise from minor adaptations of the syntheses of the related thiaflavylium, where several routes are available. One option is condensation of the intermediate 1016 with phosphorous chloride and subsequent treatment with perchloric acid. Intermediate 1016 can be achieved thorough 1,4-addition of the dimethylamino benzenethiol into styryl methyl ketone. The sulfone 1014 will be accessed by oxidation of heterocycle 1013 (Scheme 3D).

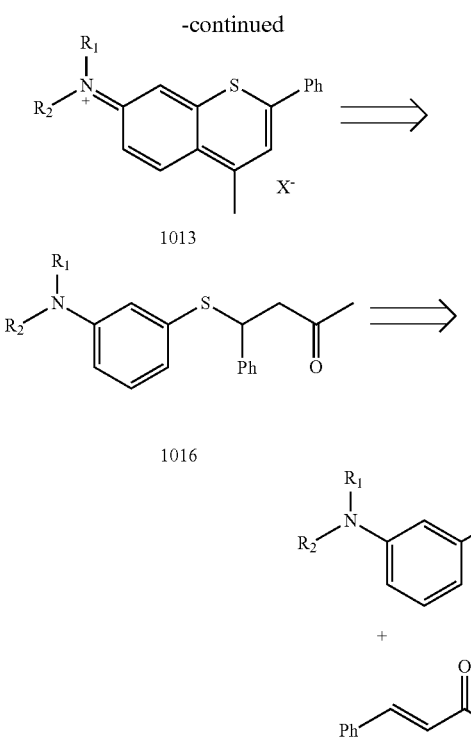

From these heterocycles, all heptamethine dyes will be achieved through the base catalyzed condensation of N[(3-(anilinomethylene)-2-chloro-1-cyclohexen-1-yl)methylene] aniline hydrochloride (2) or with N-[5-(phenylamino)-2,4-pentadien-1-ylidene]-hydrochloride or similar bis-imine or bis-aldehyde equivalents onto the activated methyl group of the heterocycle, as was described above for the synthesis of Flav7 (3). Various pentamethine dyes can be accessed through the base catalyzed condensation of malonaldehyde bis(phenylimine) mono hydrochloride or similar, as was described for the synthesis of Flav5 (4). Trimethine dyes can be accessed through the introduction of a one-carbon electrophile such as formaldehyde, paraformaldehyde, or triethyl orthoformate, as was described for the synthesis of Flav3 (5).

Asymmetric dyes (i.e., dyes containing two different heterocycles) may be prepared from a "half-dye" such as 23, the cyanine half-dye:

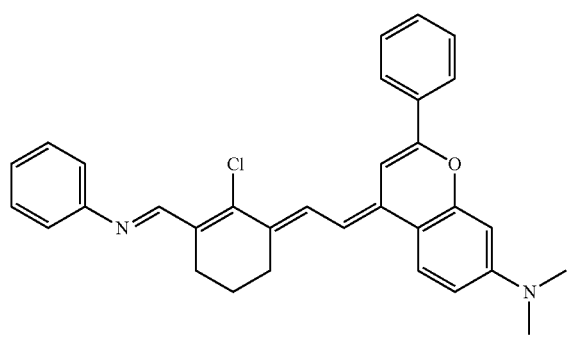

23

The half-dye can be prepared by treating the activated flavylium heterocycle with 1 equivalent of bis-imine or aldehyde equivalent (such as N-[(3-(anilinomethylene)-2-chloro-1-cyclohexen-1-yl)methylene] aniline hydrochloride) in basic conditions in an appropriate solvent (see Pisoni, D. S.; Ce, A.; Borges, A.; Petzhold, C. L.; Rodembusch, F. S.; Campo, L. F. J. Org. Chem. 2014, 79, 5511-5520.; Shi, Q. Q.; Sun, R.; Ge, J. F.; Xu, Q. F.; Li, N. J.; Lu, J. M. Dye. Pigment. 2012, 93, 1506-1511.; Miltsov, S.; Karavan, V.; Goikhman, M.; Podeshvo, I.; Gómez-De Pedro, S.; Puyol, M.; Alonso-Chamarro, J. Dye. Pigment. 2014, 109, 34-41.; Rivera, L.; Puyol, M.; Miltsov, S.; Alonso, J. Anal. Bioanal. Chem. 2007, 387, 2111-2119.) or by treatment of a polymethine dye with bases such as imidazole, dimethylamino pyridine, aniline, carbazole, or 1,8-diazabicyclo[5.4.0]undec-7-ene. The "half-dye" can be converted to various asymmetric dyes by treatment with the activated heterocycle of interest in basic conditions (see WO2008015415A2). Asymmetric polymethine dye comprising the heterocycles disclosed herein, or other suitable heterocycles, may be prepared by these and other suitable methods. For example, the following exemplary asymmetric polymethine dyes may be prepared by the methods disclosed herein:

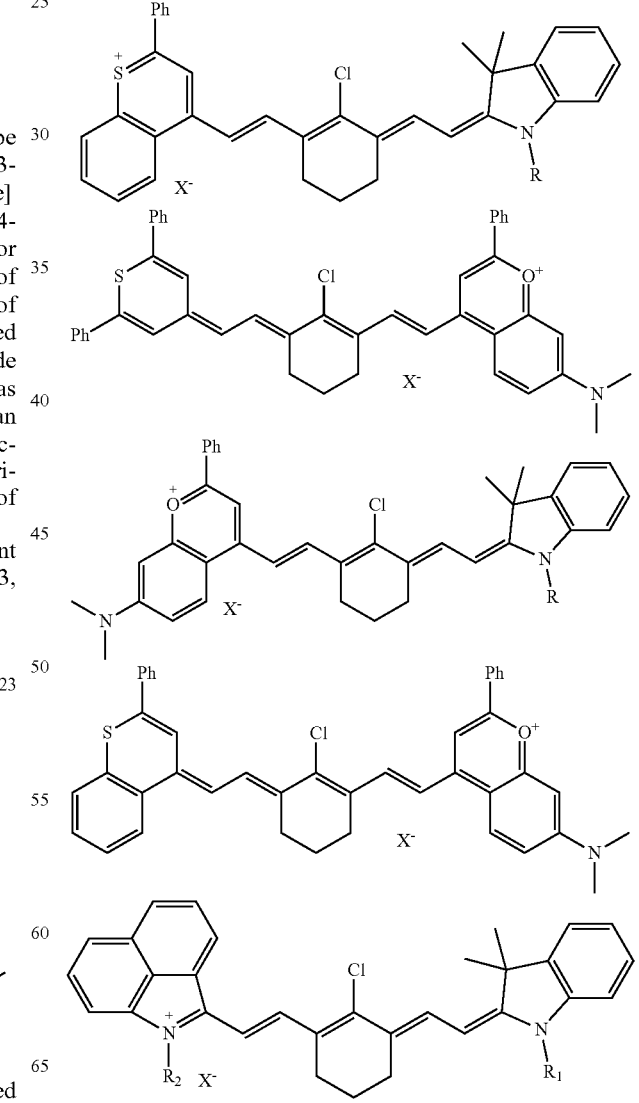

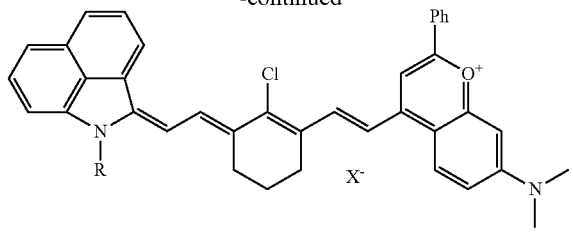

SWIR Light-Cleavable Probes as a Delivery Mechanism

The heptamethine dyes disclosed herein may be utilized to create SWIR activatable fluorescent probes, sensors, or delivery methodologies. The advantages of turn-on fluorescent probes that can be both triggered by SWIR light and detected with a SWIR detector are twofold. 1) The fluorescence imaging in the SWIR is superior in depth and resolution and 2) the reduced scattering of SWIR light and lack of competing endogenous chromophores in this region will allow a smaller intensity of light to be used to effectively deliver the energy required for activation at the desired tissue depth. This will allow faster and more complete activation. Additionally, the expansion of chemical species specific probes to the SWIR region will make possible experiments to extract more functional information about chemical environments in vivo than is currently achievable with MR chemical sensors. Accurate sensing will be improved both in its depth and resolution in the biological environment of interest. The same strategy can be used to deliver a cargo upon treatment with a defined wavelength of light.

Recently, Schnermann and coworkers have developed an elegant, singlet oxygen dependent strategy for photo-induced drug delivery with heptamethine cyanine dyes. (Gorka et al., J. Am. Chem. Soc. 2014, 136, 14153-14159, dx.doi.org/10.1021/ja5065203). This strategy can be applied to the SWIR polymethine dyes described herein. The major photobleaching mechanism of polymethines has been characterized as the reaction with singlet oxygen to form dioxetane intermediates. The dioxetane then ring opens to break the methine chain and produce two carbonyls. In order to employ this cleavage for photo-uncaging, heptamethine cyanine derivatives with a tertiary amine at the central methine position were used. This amine attaches the photolabile dye to a caged substrate (such as a therapeutic cargo, or another dye) through a cleavable linker.

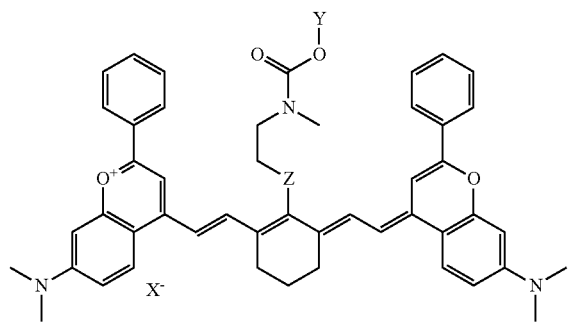

In the structure depicted above, Y is a cargo moiety; Z is N(R) or S, and R is alkyl.

Upon photooxidation, hydrolysis occurs due to the increased imine character in the C—N bond at the central methine position. The linker is then designed to undergo an intramolecular cyclization with nucleophilic attack into the carbamate to release the cargo. Here, a photolabile SWIR dye will serve as the photocleavable group and the caged compound to be released may be either a more photostable dye or another cargo.

Figure 4A:
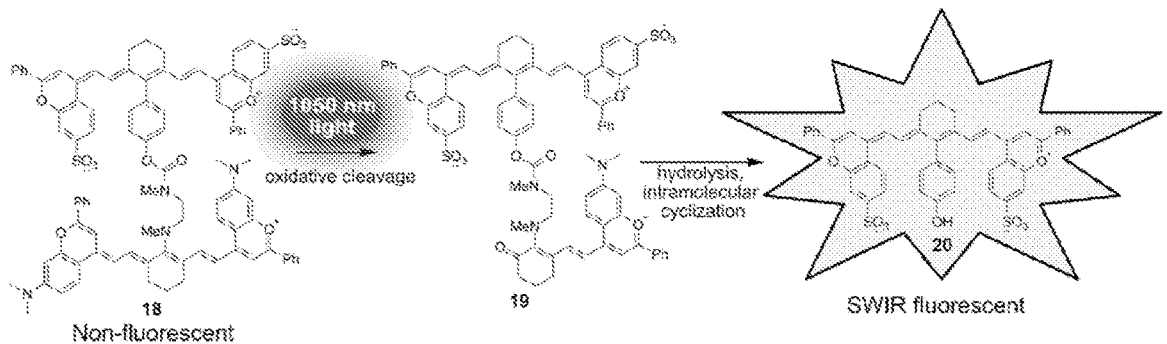
FIGS. 4A and 4B shows schematic depictions of cargo release according to methods described herein.

When the cargo is a dye, the two dyes' close proximity will cause a desired florescence quenching. However, upon release of the caged dye, fluorescence will be restored (FIG. 4). Dyes with electron withdrawing groups, (e.g. sulfates), will generally have a much slower reactivity with singlet oxygen and other ROS, and thus a severely reduced photobleaching rate, due to their more electron poor polymethine chain. The sulfate dye derivatives disclosed above may thus be used as the caged fluorophore (the cargo) and a more photolabile dyes with amine functionality will compose the SWIR cleavable dye (the carrier). A key design feature is that the excitation of the photolabile dye must be at a longer wavelength than the caged dye absorbs, such that the wavelength used for probe cleavage will be distinct from the excitation wavelength of the uncaged fluorophore. This relationship should come naturally to this probe design, as heptamethine dyes with electron donating groups will generally absorb longer wavelength light than those with electron withdrawing substituents. For example, we have previously measured the photostabilities for dyes 1-4 using a 532 nm laser. While Flav1, Flav3 and Flav5 display extremely high photostabilities for fluorophores at their respective wavelength region (Flav3 is 4x as photostable as the 7-cyanine 1,1',3,3,3',3'-hexamethylindotricarbocyanine iodide, (HITCI, FIG. S5), Flav7 is significantly more photolabile. Thus, in such a system, Flav7 may be used as the carrier, i.e., photocleavable dye, and another, more photostable dye could be used as the cargo, i.e., the dye that is to be released and detected.

In some embodiments, the cargo may be a drug product that has a phenol moiety and is capable of being attached to a polymethine dye as described. For example, doxorubicin, gemcitabine, and paclitaxel may be used as cargos.

In some embodiments, this approach may be employed in combination with PFC nanoemulsions. A fluorous soluble polymethine as disclosed herein may act as the fluorous tag for the cargo, which may be incorporated into a fluorous emulsion. Upon irradiation with SWIR light, photodissociation will occur and the cargo will be released from the fluorous tag. The cargo will no longer be fluorous soluble and will be readily ejected from the emulsion.

Figure 4B:
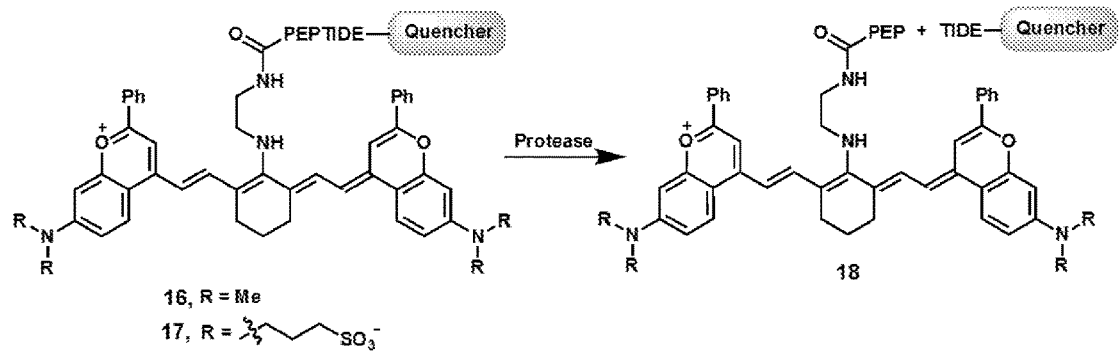
Figure 5A:
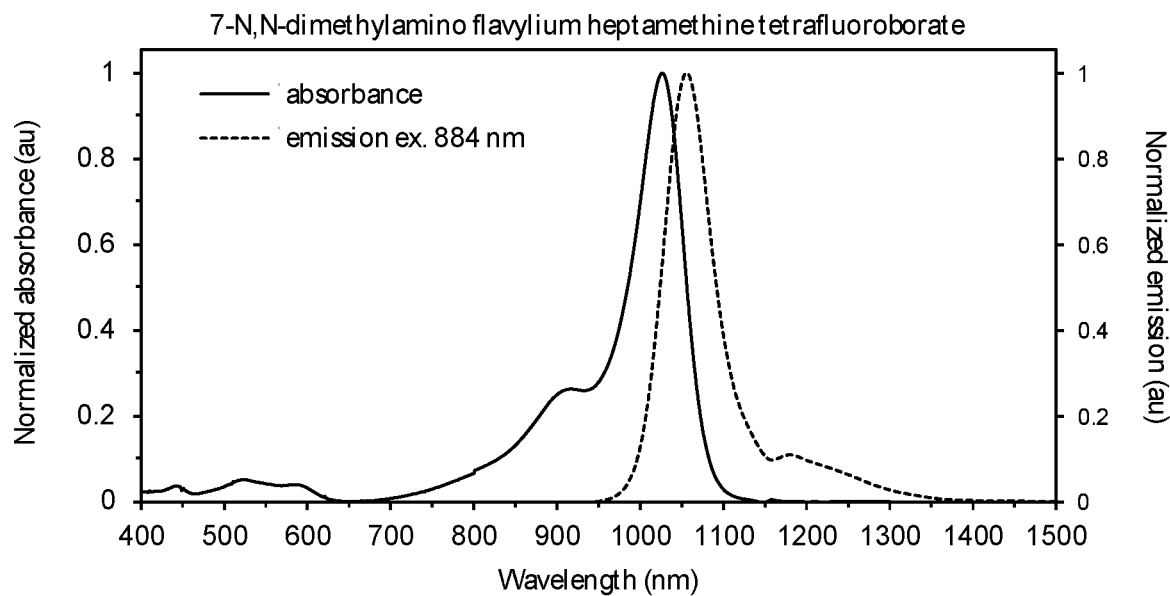
FIGS. 5A-5G show normalized absorption and emission spectra for exemplary compounds of the present disclosure.
Figure 5B:
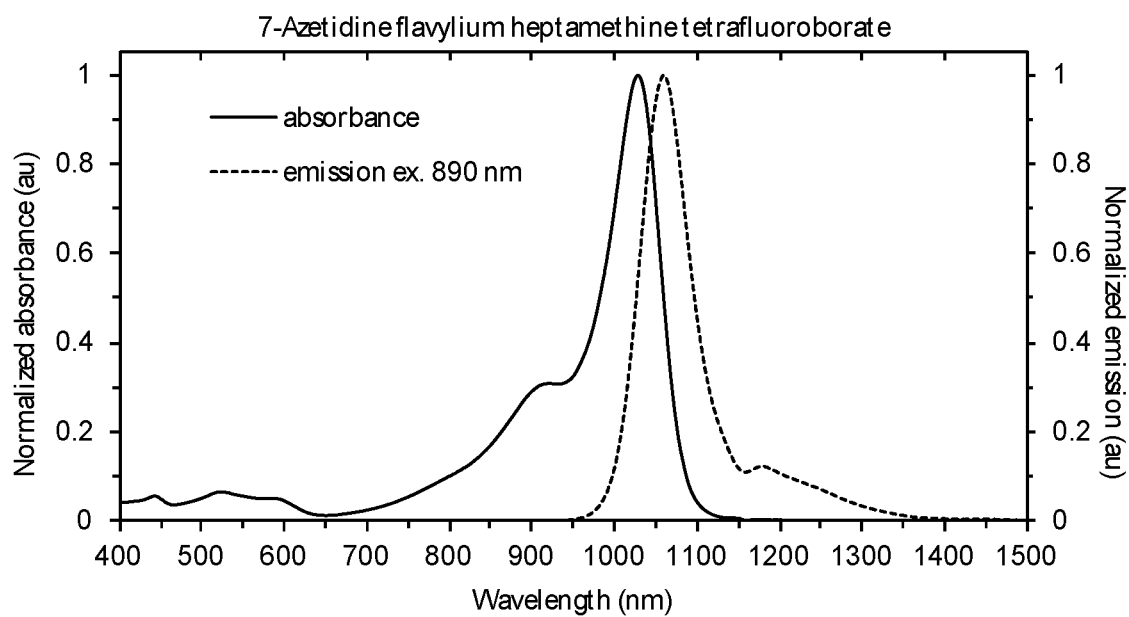
Figure 5C:
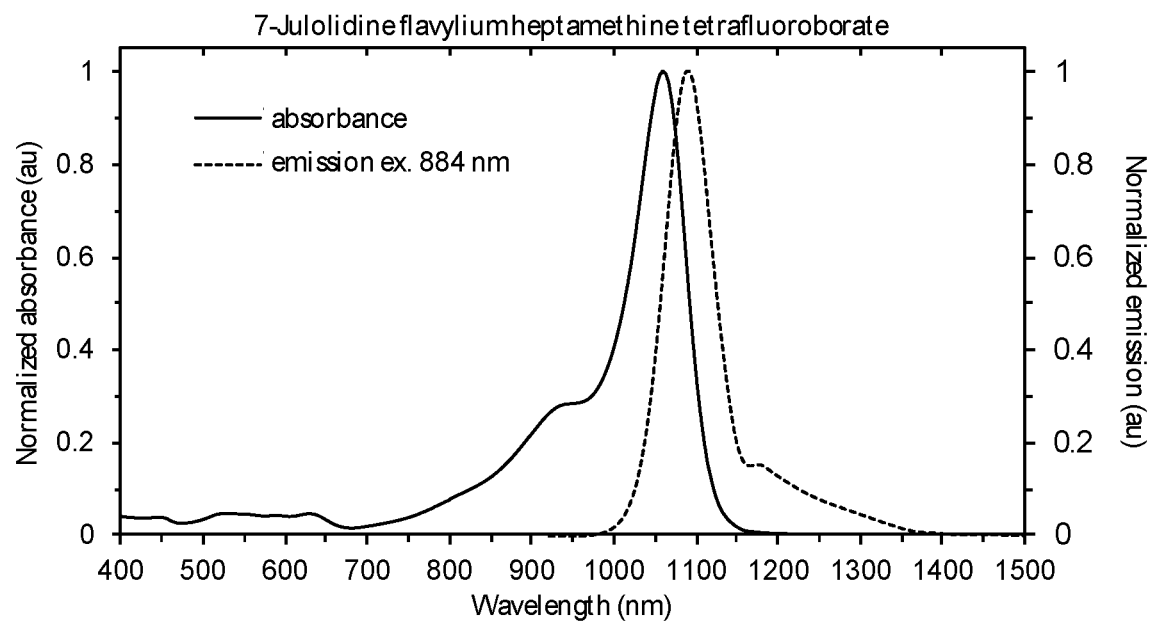
Figure 5D:
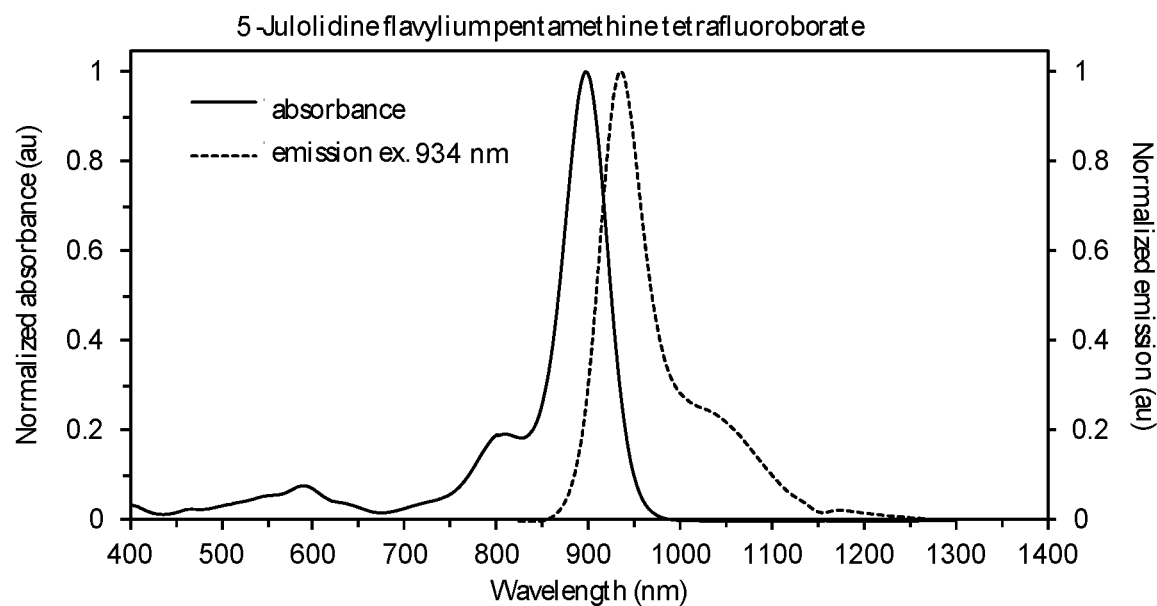
Figure 5E:
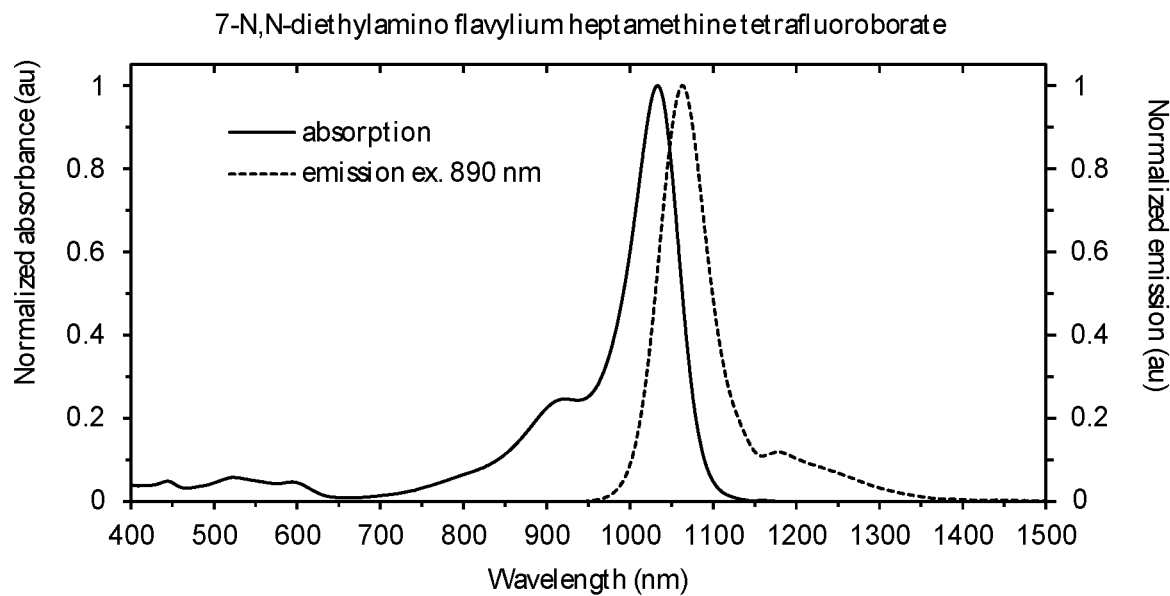
Figure 5F:
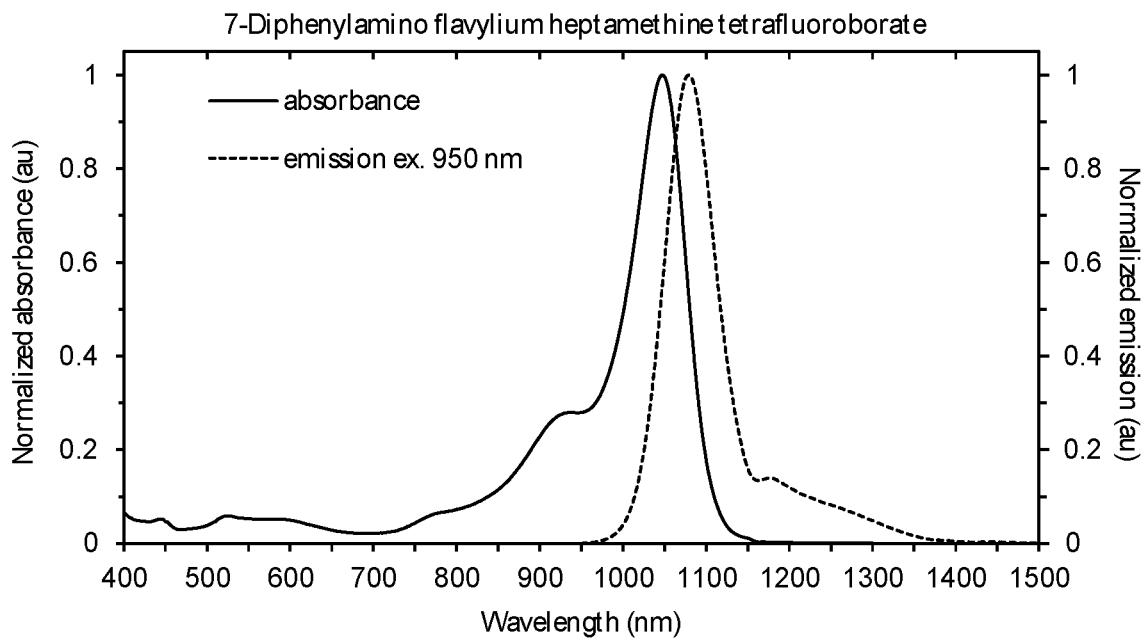
Figure 5G:
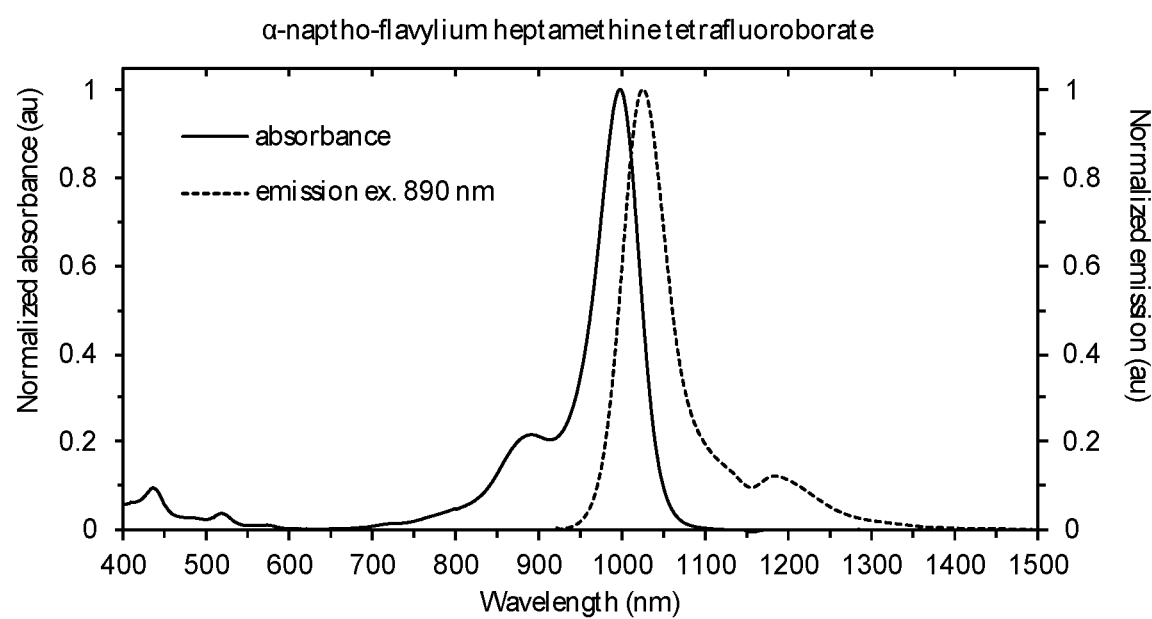

In some embodiments, a polymethine dye as disclosed herein may be linked via a peptide to a MR-II quencher (FIG. 4B). The peptide will be engineered to include the cleavage sequence for MMP8, a protease often upregulated in breast cancer.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

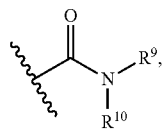

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

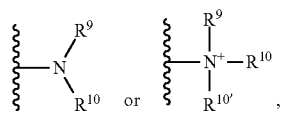

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

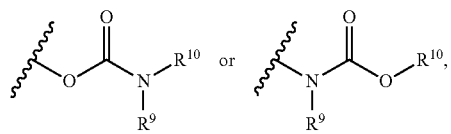

wherein $R^9$ and $R^{10}$ independently represent hydrogen or a hydrocarbyl group.

The term "carbocyclylalkyl", as used herein, refers to an alkyl group substituted with a carbocycle group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —$C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

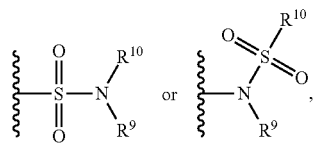

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

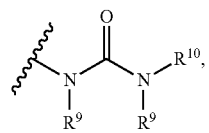

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient (e.g., dye) which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds (e.g., dyes) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid-addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

The invention now being generally described, it will be more readily understood by reference to the following examples which are included merely for purposes of illustration of certain aspects and embodiments of the present invention, and are not intended to limit the invention.

Example 1: Preparation of Dimethylaminoflavylium Dyes

7-Dimethylamino flavylium heptamethine dye (3, Flav7): 4-((E)-2-((E)-2-chloro-3-(2-((E)-7-(dimethylamino)-2-phenyl-4H-chromen-4-ylidene)ethylidene)cyclohex-1-en-1-yl) vinyl)-7-(dimethylamino)-2-phenylchromenylium perchlorate 7-N,N-dimethylamino-4-methyl-flavylium perchlorate (1) (31.1 mg, 0.0855 mmol, 2.1 equiv), N-[(3-(anilinomethylene)-2-chloro-1-cyclohexen-1-yl)methylene]aniline 6 (13.0 mg, 0.040 mmol, 1.0 equiv.) and anhydrous sodium acetate (9 mg, 0.1 mmol, 2.5 equiv.) were dissolved in EtOH (0.78 mL, anhydrous) and heated to 90° C. for 6 hours. The solution was cooled to room temperature and evaporated onto silica gel. Dye 3 was purified via silica gel chromatography, eluting with a DCM/MeOH solvent gradient of 200:1, 150:1, 100:1, 80:1, 67:1 and 50:1. This procedure gave pure 3 (11.1 mg, 0.0145 mmol, 36%). 1H NMR (500 MHz, DMSO-d6): δ 8.21 (d, J=10 Hz, 2H), 8.14-8.10 (m, 6H), 7.70-7.53 (m, 8H), 7.06 (d, J=15 Hz, 2H), 6.96 (dd, J=10 Hz, 2.5 Hz, 2H), 6.81 (d, J=2.5 Hz, 2H), 3.14 (s, 12H), 2.87-2.81 (m, 4H), 1.91 (t, J=6.3 Hz, 2H). 13C NMR (126 MHz, DMSO-d6): δ 156.9, 155.9, 154.6, 145.0, 144.5, 138.5, 132.0, 131.6, 131.3, 129.6, 126.7, 126.5, 113.9, 113.8, 112.4, 102.3, 97.9, 27.2, 21.3, {peak at 38.9-40.1 beneath DMSO-d6 solvent peak}. HRMS (ESI+): Calculated for C44H40ClN2O2+[M]+: 663.2773; found: 663.2784. Absorbance (DCM): 522 nm ($\varepsilon$=1.5±0.2×10$^4$ M$^{-1}$ cm$^{-1}$), 916 nm ($\varepsilon$=6.3±0.1×10$^4$ M$^{-1}$ cm$^{-1}$), 1026 nm ($\varepsilon$=2.4±0.2×10$^5$ M$^{-1}$ cm$^{-1}$). Emission (DCM, Ex. 730 nm): 1045 nm, $\Phi_F$=0.53±0.03%.

7-Dimethylamino flavylium pentamethine dye (4, Flav5): 7-(dimethylamino)-4-41E,3E)-5-((E)-7-(dimethylamino)-2-phenyl-4H-chromen-4-ylidene)penta-1,3-dien-1-yl)-2-phenylchromenylium perchlorate 7-N,N-dimethylamino-4-methyl-flavylium perchlorate[2] (1) (29.8 mg, 0.0819 mmol, 2.1 equiv), malonaldehyde bis(phenylimine) (10.2 mg, 0.0394 mmol, 1.0 equiv.), and anhydrous sodium acetate (9 mg, 0.1 mmol, 2.7 equiv.) were combined in acetic anhydride (0.66 mL). The solution was freeze-pump-thawed three times and subsequently heated at 110° C. for 2.5 h. The solution was let cool to room temperature and evaporated onto silica gel. Dye 4 was purified via silica gel chromatography, eluting with a DCM/MeOH solvent gradient of 200:1, 167:1, 143:1, 125:1, 111:1, 100:1, 67:1. The procedure yielded pure 4 (13.1 mg, 0.0198 mmol, 50%). 1H NMR (500 MHz, DMSO-d$_6$): δ 8.2 (t, J=12.8 Hz, 2H), 8.11-8.03 (m, 4H), 7.98 (d, J=9.4 Hz, 2H), 7.66 (s, 2H), 7.61-7.52 (m, 6H), 7.07 (d, J=13.2 Hz, 2H), 6.94-6.86 (dd, J=9.2, 1.5 Hz, 2H), 6.82 (t, J=12.3 Hz, 1H), 6.77 (s, 2H), 3.13 (s, 12H). 13C NMR (126 MHz, DMSO-d$_6$): δ 156.3, 155.4, 154.2, 149.1, 145.7, 131.6, 131.2, 129.1, 126.1, 125.9, 115.3, 113.2, 110.9, 101.6, 97.4, {peak at 38.9-40.1 beneath DMSO-d$_6$ solvent peak}. HRMS (ESI$^+$): Calculated for $C_{39}H_{35}N_2O_2^+$[M]$^+$: 563.2693; found: 563.2702. Absorbance (DCM): 546 nm ($\varepsilon$=1.4±0.1×10$^4$ M$^{-1}$ cm$^{-1}$), 776 nm ($\varepsilon$=4.8±0.4×10$^4$ M$^{-1}$ cm$^{-1}$), 862 nm ($\varepsilon$=2.4±0.2×10$^5$ M$^{-1}$ cm$^{-1}$). Emission (DCM, Ex. 840 nm): 908 nm, $\Phi_F$=5±2%.

7-Dimethylamino flavylium trimethine dye (5, Flav3): 7-(dimethylamino)-4-((E)-3-((E)-7-(dimethylamino)-2-phenyl-4H-chromen-4-ylidene)prop-1-en-1-yl)-2-phenyl-chromenylium perchlorate 7-N,N-dimethylamino-4-methyl-flavylium perchlorate[2] (1) (49.8 mg, 0.137 mmol, 1.5 equiv.), paraformaldehyde (2.7 mg, 0.090 mmol, 1.0 equiv.), and anhydrous sodium acetate (15 mg, 0.18 mmol, 2.0 equiv) were combined in acetic anhydride (1.0 mL). The solution was freeze-pump-thawed three times and heated at 70° C. for 30 m. The solution was cooled to room temperature and evaporated onto silica gel. Dye 5 was purified via silica gel chromatography, eluting with a DCM/EtOH solvent gradient of 200:1, 167:1, 143:1, 125:1, 111:1, 100:1. The most pure fractions, as determined by UV-Vis/IR spectroscopy were loaded onto a second silica gel column and run as before. The impure fractions from both columns were combined and run on another silica gel column with the same solvent system and gradient. This procedure yielded pure 5 (15.5 mg, 0.0243 mmol, 27%). 1H NMR (500 MHz, DMSO-d$_6$): δ 8.81 (t, J=12.9 Hz, 1H), 8.18-8.10 (m, 4H), 7.99 (s, 2H), 7.89 (d, J=9.6 Hz, 2H), 7.67-7.57 (m, 6H), 7.16 (d, J=13.0 Hz, 2H), 6.91 (dd, J=9.3, 2.5 Hz, 2H), 6.72 (d, J=2.5 Hz, 2H), 3.12 (s, 12H). 13C NMR (126 MHz, DMSO-d$_6$) δ 156.7, 155.4, 154.2, 147.2, 145.5, 131.6, 131.1, 129.0, 126.4, 125.5, 115.9, 113.2, 110.6, 102.0, 97.1, {peak at 38.9-40.1 beneath DMSO-d$_6$ solvent peak}. HRMS (ESI$^+$): Calculated for $C_{37}H_{33}N_2O_2^+$[M]$^+$: 537.2537; found: 537.2525. Absorbance (DCM): 530 nm ($\varepsilon$=2.0±0.1×10$^4$ M$^{-1}$ cm$^1$), 682 nm ($\varepsilon$=3.9±0.2×10$^4$ M$^{-1}$ cm$^1$), 746 ($\varepsilon$=2.2±0.1×10$^5$ M$^{-1}$ cm$^{-1}$). Emission (DCM, Ex. 675 nm): 766 nm, $\Phi_F$=2.9±0.5%.

7-Dimethylamino flavylium monomethine dye (6, Flav1): (E)-7-(dimethylamino)-4-((7-(dimethylamino)-2-phenyl-4H-chromen-4-ylidene)methyl)-2-phenylchromenylium 2,2,2-trifluoroacetate (6) 7-N,N-dimethylamino-4-methyl-flavylium perchlorate[2] (1) (49.7 mg, 0.137 mmol, 1 equiv.) and anhydrous sodium acetate (25 mg, 0.31 mmol, 2.2 equiv) were dissolved in 10 mL EtOH and refluxed at 90° C. under air for 3.3 h. The mixture was cooled to rt and evaporated onto silica gel. Dye 6 was purified via silica gel chromatography and reverse-phase HPLC. Via silica gel chromatography, dye 6 was eluted with a DCM/MeOH solvent gradient of 400:1, 200:1, 167:1, 143:1, 125:1, 111:1, 67:1, and 33:1. The most pure fractions were further purified in aliquots by HPLC in a water/MeCN with 0.1% TFA solvent mixture. The method used is as follows: 70:30 for 2 m, gradient to 30:70 over 60 m, gradient to 5:90 over 20 m, followed by a hold for 5 m and subsequent re-equilibration to 70:30 for 10 m. The procedure yielded pure 6 (9.5 mg, 0.016, 11%). $^1$H NMR (500 MHz, DMSO-$d_6$): δ 8.40 (d, J=10.5 Hz, 2H), 8.17 (dd, J=8.0, 1.7 Hz, 4H), 7.98 (s, 2H), 7.66-7.59 (m, 6H), 7.47 (s, 1H), 7.10 (dd, J=9.4, 2.6 Hz, 2H), 6.99 (d, J=2.6 Hz, 2H), 3.21 (s, 12H). $^{13}$C NMR (126 MHz, DMSO-$d_6$) δ 158.96, 158.63, 158.39, 158.15, 157.90, 156.31, 155.19, 150.61, 132.60, 131.54, 129.76, 127.63, 126.97, 121.43, 119.03, 116.64, 115.01, 114.06, 112.09, 105.40, 103.64, 97.71 {peak at 38.9-40.1 beneath DMSO-$d_6$ solvent peak}. $^{19}$F NMR (282 MHz, DMSO-$d_6$) δ −73.16. HRMS (ESI$^+$): Calculated for $C_{35}H_{31}N_2O_2^+$[M]$^+$: 511.2380; found: 511.2366. Absorbance (DCM): 324 nm (ε=3.±1.×10$^3$ M$^{-1}$ cm$^{-1}$), 484 nm (ε=3.±1.×10$^3$ M$^{-1}$ cm$^{-1}$), 514 nm (ε=4.±1.×10$^3$ M$^{-1}$ cm$^{-1}$), 650 nm (ε=1.6±0.5×10$^4$ M$^{-1}$ cm$^{-1}$). Emission (DCM, Ex. 610 nm): 684 nm, $\Phi_F$=0.7±0.5%.

Example 2: Spectra of Dimethylaminoflavylium Dyes

The absorbance spectra in FIG. 2 and FIG. 5 were obtained in DCM on a JASCO V-770 UV-Visible/MR spectrophotometer with a 2000 nm/min or 4000 nm/min scan rate. Plotted are the baseline corrected and normalized data. The emission spectra in FIG. 2 were taken in DCM on either a Horiba Instruments PTI QuantaMaster Series fluorometer (6), a Fluoromax-3 spectrofluorometer (1, 3-5), or home-built InGaAs array detector (Princeton Instruments). For 6 the following parameters were used: ex. 610 nm, emission collected from 620-900 nm, slits 5 nm, step size 1 nm, integration time 1 s. Plotted is the DCM corrected, baseline corrected, normalized data. For 1, and 3-5, the following parameters were used: slits 5 nm, step size 1 nm, integration time, 0.25 s. Excitation values and emission collection were as follows: 1 (ex. 460, collection 470-800 nm), 5 (ex. 675 nm, collection 685-950 nm), 4 (ex. 840 nm, emission 850-1100 nm), 3 (ex. 730 nm, emission 950-1400). Plotted are the baseline corrected, normalized data. The emission spectra in FIG. 5 were taken in dichloromethane on a Horiba Instruments QuantaMaster Series fluorometer with excitation slits: 15 nm, emission slits: 30 nm, step size: 1 nm, integration time: 0.1 s and excitation wavelengths as indicated.

Figure 3A:
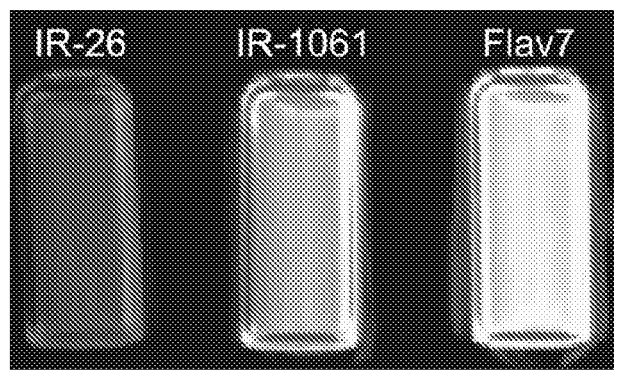
FIG. 3A shows images of vials of IR-26, IR-1061 and Flav7 with matched optical density at 808 nm in dichloromethane, excited at 808 nm, collected using an InGaAs camera (1000-1500 nm).
Figure 3B:
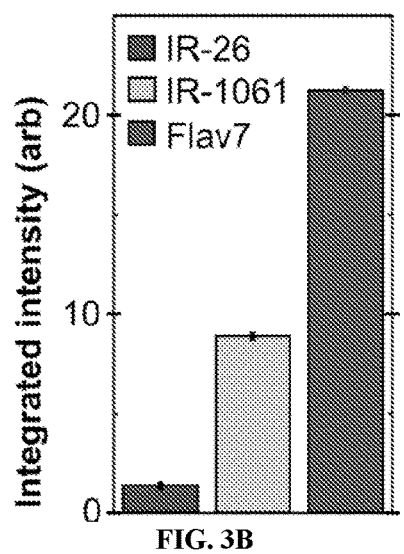
FIG. 3B shows the average background subtracted camera intensity for ten frames normalized to exposure.

For FIGS. 3A and 3B, Flay 7 3, IR-26, and IR-1061 were diluted in DCM until matching absorbance was achieved at 808 nm. Spatially dispersed 808 nm illumination was used to image 1 ml samples in 2.5 mL cuvettes of the SWIR dyes alongside a DCM blank. Each dye was compared at the same position to ensure consistent camera illumination. SWIR images were collected on an InGaAs camera (Princeton Instruments, NIRvana 640) with a 1000 nm long-pass filter. The camera was cooled to −80° C., the analog to digital (AD) conversion rate set to 2 MHz, the gain set to high, and different exposure times used to achieve sufficient signal and/or frame rates. All images were background- and blemish-corrected within the LightField imaging software. All analysis was performed using ImageJ and Matlab (Mathworks). Bar graph intensities were taken as the average camera intensity for 10 frames, background corrected to the DCM blank, with the error corresponding to standard deviation.

Example 3: Preparation of Extended Flavylium Compounds

Exemplary extended flavylium heterocycles may be prepared by a person of ordinary skill in the art from commercially available reagents by following Scheme 4, 5, or 6:

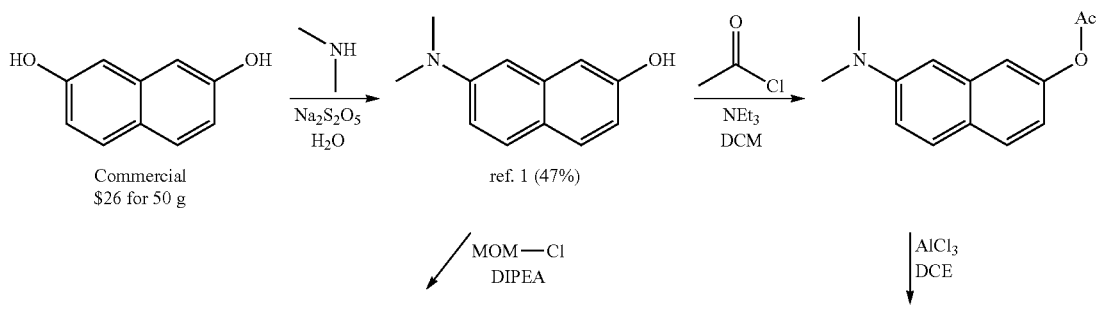

Scheme 4

53
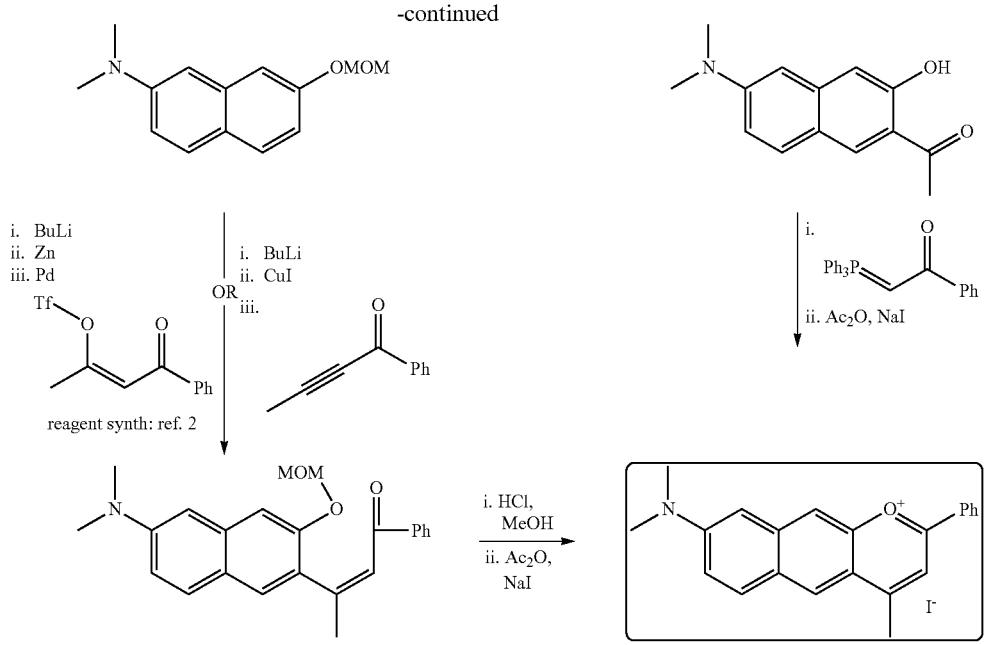
1. Talanta, 2015, 132, 727-732
2. *J. Org. Chem.* 2008, 73, 7845-7848.
Scheme 5
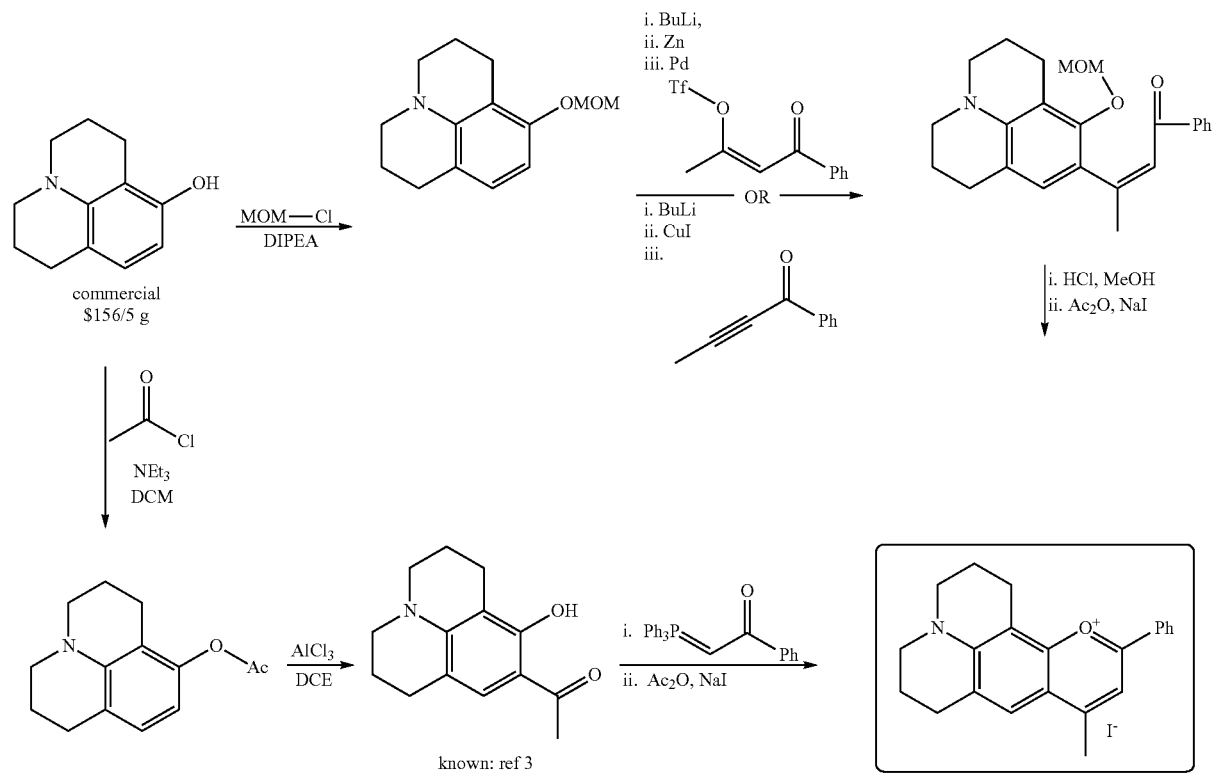
3. JP 03133988 (1991)

Scheme 6
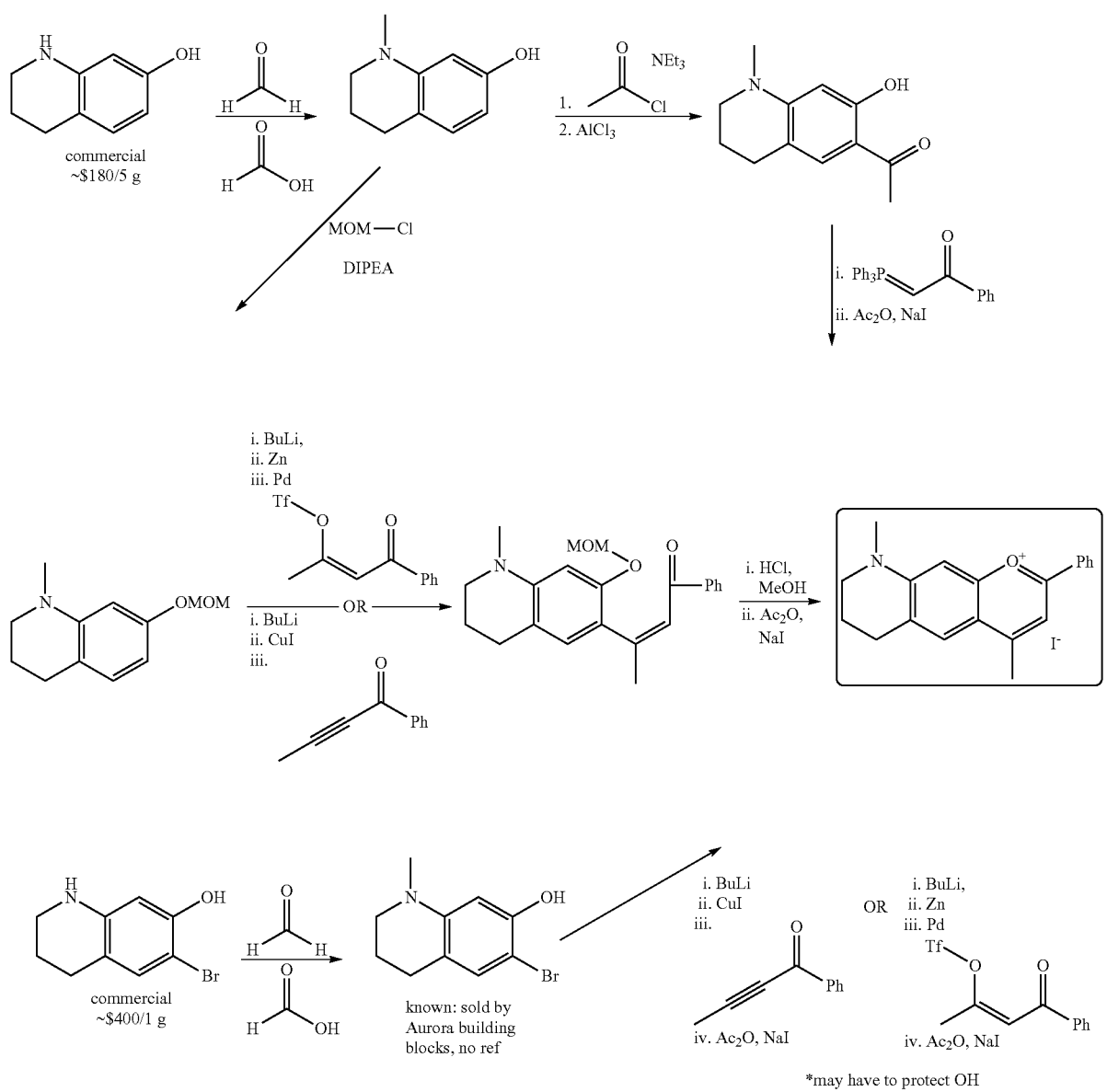
Symmetric polymethine dyes may be prepared from their respective heterocycles, for example, by the procedure of Scheme 7.
Scheme 7
-continued
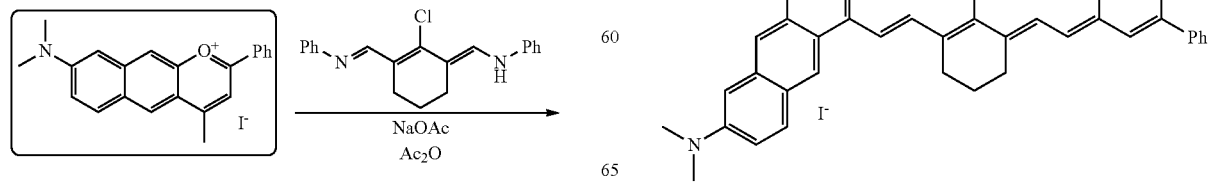

Example 4

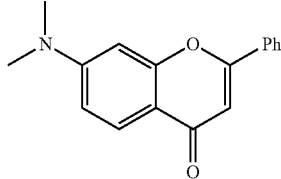 [SMILES: CN(C)c1ccc2c(=O)cc(-c3ccccc3)oc2c1]

7-N,N-dimethylamino-flavone (7-(dimethylamino)-2-phenyl-4H-chromen-4-one). 3-dimethylaminophenol (500 mg, 3.64 mmol, 1 equiv.) and ethyl benzoylacetate (1.10 mL, 6.37 mmol, 1.75 equiv.) were combined in a 10 mL flask and heated at 180° C. for 24 h. The solution was cooled to room temperature, evaporated onto silica gel and purified via column chromatography with a 50:1 to 1:4, followed by a 6:1 to 1:1 hexanes: ethyl acetate gradient. The procedure gave a beige solid (493 mg, 1.86 mmol, 51%). $^1$H NMR (500 MHz, Chloroform-d) δ 8.01 (d, J=9.0 Hz, 1H), 7.93-7.84 (m, 2H), 7.51-7.44 (m, 3H), 6.73 (dd, J=9.0, 2.4 Hz, 1H), 6.67 (s, 1H), 6.55 (d, J=2.4 Hz, 1H), 3.07 (s, 6H). $^{13}$C NMR (126 MHz, Chloroform-d) δ 177.94, 162.26, 158.45, 154.23, 132.34, 131.11, 128.97, 126.60, 126.11, 113.70, 110.87, 107.31, 40.26. MS (ESI$^+$): calculated for $C_{17}H_{16}NO_2^+$[M+H]$^+$: 266.3; found: 266.1. Absorbance (CH$_2$Cl$_2$): 229 nm, 274 nm, 358 nm.

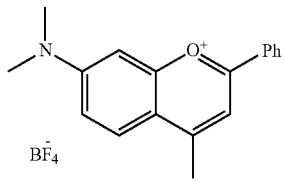

7-N,N-dimethylamino-4-methyl-flavylium tetrafluoroborate (7-(dimethylamino)-4-methyl-2-phenylchromenylium tetrafluoroborate). 7-N,N-dimethylamino-flavone (309 mg, 1.17 mmol, 1.0 equiv.) was dissolved in 10 mL THF in a 25 mL flame dried 2-neck flask and cooled to 0° C. Dropwise addition of methyl magnesium bromide (1.4 M in THF/toluene, 1.30 mL, 1.56 equiv.) was followed by stirring at room temperature overnight. The resulting solution was poured onto ice, extracted into DCM, washed with 5% aqueous HBF$_4$, dried with MgSO$_4$, decanted, and evaporated. The crude product was purified by precipitation in hot EtOAc to yield a dark red solid (189.8 mg, 0.539 mmol, 46%). $^1$H NMR (600 MHz, DMSO-d$_6$) δ 8.44-8.34 (m, 2H), 8.23 (s, 1H), 8.21 (d, J=9.6 Hz, 1H), 7.81-7.75 (m, 1H), 7.74-7.67 (m, 2H), 7.51 (dd, J=9.6, 2.5 Hz, 1H), 7.35 (d, J=2.5 Hz, 1H), 3.35 (s, 6H), 2.89 (s, 3H). $^{13}$C NMR (126 MHz, Acetone-d$_6$) δ 166.22, 165.16, 159.90, 159.13, 135.07, 130.70, 130.64, 129.68, 128.68, 119.22, 118.98, 112.97, 97.06, 41.26, 20.00. MS (ESI$^+$): calculated for $C_{18}H_{18}NO^+$[M]$^+$: 264.1; found: 264.0. Absorbance (CH$_2$Cl$_2$): 238 nm, 294 nm, 338 nm, 510 nm. Emission (CH$_2$Cl$_2$, ex. 500 nm): 589 nm.

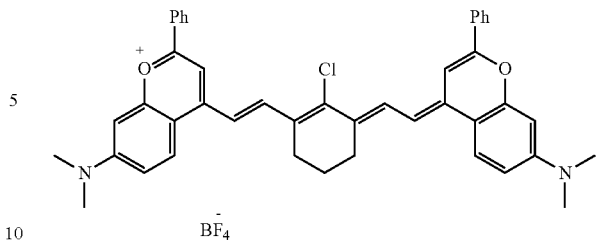

7-N,N-dimethylamino flavylium heptamethine tetrafluoroborate (4-((E)-2-((E)-2-chloro-3-(2-((E)-7-(dimethylamino)-2-phenyl-4H-chromen-4-ylidene)ethylidene)cyclohex-1-en-1-yl)vinyl)-7-(dimethylamino)-2-phenylchromenylium tetrafluoroborate): 7-N,N-dimethylamino-4-methyl-flavylium tetrafluoroborate (131 mg, 0.374 mmol, 1.0 equiv), N-[(3-(anilinomethylene)-2-chloro-1-cyclohexen-1-yl)methylene]aniline hydrochloride (64.5 mg, 0.180 mmol, 0.48 equiv.), and sodium acetate (90.0 mg, 1.10 mmol, 2.9 equiv.) were dissolved in 2.1 mL n-butanol and 0.9 mL toluene (7:3 mixutre of n-butanol: toluene) in a flame dried Schleck flask under N$_2$ atmosphere. The solution was freeze-pumped thawed ×3 and heated to 100° C. for 15 min. The crude mixture was evaporated and purified by column chromatography (dry load), with dichloromethane and a gradient of 0.5% to 10% ethanol. The procedure yielded a dark purple solid (68.2 mg, 0.0909 mmol, 51%). $^1$H NMR (500 MHz, DMSO-d$_6$) δ 8.23 (d, J=13.6 Hz, 2H), 8.22-8.11 (m, 6H), 7.69 (s, 2H), 7.63-7.54 (m, 6H), 7.11 (d, J=13.9 Hz, 2H), 7.01 (dd, J=9.3, 2.4 Hz, 2H), 6.87 (d, J=2.5 Hz, 2H), 3.17 (s, 12H), 2.94-2.79 (m, 4H), 1.94-1.84 (m, 2H). MS (ESI$^+$): calculated for $C_{44}H_{40}ClN_2O_2^+$[M]$^+$: 663.3; found: 663.2. Absorbance (CH$_2$Cl$_2$): 522 nm, 916 nm, 1026 nm. Emission (CH$_2$Cl$_2$, ex. 884 nm): 1054 nm.

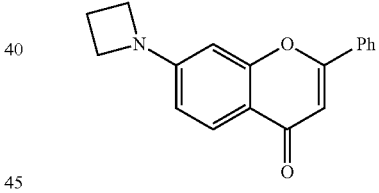

7-Azetidine-flavone (7-(azetidin-1-yl)-2-phenyl-4H-chromen-4-one): 7-trifluoromethanesulfonate-flavone (4-oxo-2-phenyl-4H-chromen-7-yl trifluoromethanesulfonate) (58.5 mg, 0.158 mmol, 1.0 equiv.), RuPhos-Pd-G3 (12.8 mg, 0.015 mmol, 0.1 equiv), RuPhos (7.2 mg, 0.015 mmol, 0.1 equiv.), and cesium carbonate (72.6 mg, 0.223 mmol, 1.4 equiv,) were added to a 15 mL flame-dried 2-neck flask, dissolved in THF (0.80 mL), and stirred at 50° C. under N$_2$ atmosphere for 5.5 h. Azetidine (34 µL, 0.504 mmol, 2.8 equiv.) was added by two 17 µL portions, initially and after 2.5 h. The reaction mixture was extracted with dichloromethane/water, dried with MgSO$_4$, filtered, and evaporated. The crude product was purified with a 10:1 to 2:1 hexanes: ethyl acetate solvent gradient to yield a yellow solid (26.7 mg, 0.100 mmol, 63%). $^1$H NMR (600 MHz, Chloroform-d) δ 8.00 (d, J=8.7 Hz, 1H), 7.92-7.78 (m, 2H), 7.54-7.40 (m, 3H), 6.68 (s, 1H), 6.40 (dd, J=8.7, 2.2 Hz, 1H), 6.26 (d, J=2.2 Hz, 1H), 4.01 (t, J=7.4 Hz, 4H), 2.43 (p, J=7.3 Hz, 2H). MS (ESI$^+$): calculated for $C_{18}H_{16}NO_2^+$[M+H]$^+$: 278.1; found: 277.8. Absorbance (CH$_2$Cl$_2$): 227 nm, 272 nm, 307 nm, 355 nm.

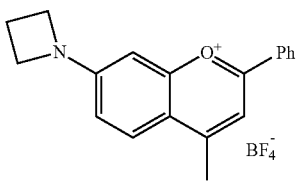

7-Azetidine-4-methyl-flavylium tetrafluoroborate (7-(azetidin-1-yl)-4-methyl-2-phenylchromenylium tetrafluoroborate): 7-Azetidine-flavone (24.7 mg, 0.089 mmol, 1.0 equiv.) was dissolved in 1.4 mL THF in a flame-dried 15 mL 2-neck flask and cooled to 0° C. Methyl magnesium bromide (1.04M in THF/toluene, 238 μL, 2.8 equiv.) was added dropwise and the resulting solution was let warm to rt and stirred overnight. The reaction was quenched with 5% aqueous $HBF_4$, and with additional water, extracted with dichloromethane, dried with $MgSO_4$, filtered, and evaporated. The crude product was purified by precipitation in ethyl acetate and filtration to yield a red solid (12.5 mg, 0.04 mmol, 39%). $^1$H NMR (400 MHz, Acetone-$d_6$) δ 8.40-8.30 (m, 2H), 8.24 (d, J=9.3 Hz, 1H), 8.08 (s, 1H), 7.81-7.73 (m, 1H), 7.73-7.64 (m, 2H), 7.14 (dd, J=9.3, 2.2 Hz, 1H), 6.94 (d, J=2.2 Hz, 1H), 4.65-4.42 (m, 4H), 2.95 (s, 3H), 2.64 (p, J=7.7 Hz, 2H). MS (ESI$^+$): calculated for $C_{19}H_{18}NO^+[M]^+$: 276.1; found: 276.0. Absorbance ($CH_2Cl_{12}$): 242 nm, 293 nm, 336 nm, 511 nm. Emission ($CH_2Cl_{12}$, ex. 500 nm): 590 nm.

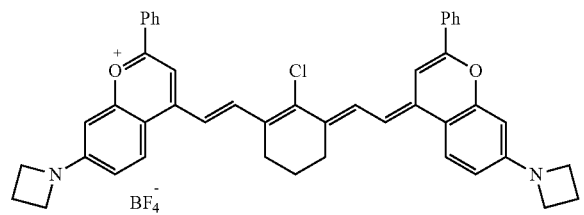

7-Azetidine flavylium heptamethine tetrafluoroborate (7-(azetidin-1-yl)-4-((E)-2-((E)-3-(2-((E)-7-(azetidin-1-yl)-2-phenyl-4H-chromen-4-ylidene)ethylidene)-2-chlorocyclohex-1-en-1-yl)vinyl)-2-phenylchromenylium tetrafluoroborate): 7-Azetidine-4-methyl-flavylium tetrafluoroborate (12.4 mg, 0.034 mmol, 1.0 equiv.), N-[(3-(anilinomethylene)-2-chloro-1-cyclohexen-1-yl)methylene]aniline hydrochloride (5.8 mg, 0.016 mmol, 0.47 equiv.), and sodium acetate (9.3 mg, 0.113 mmol, 3.3 equiv.) were added to a flame dried 1 mL vial and dissolved in 300 uL of a 7:3 mixture of n-butanol:toluene under an $N_2$ atmosphere. The reaction mixture was freeze-pump-thawed ×3, and heated to 100° C. for 10 min. The crude mixture was evaporated onto silica gel and purified via column chromatography with dichloromethane and a gradient of 0.5% to 6% ethanol, followed by a second column with dichloromethane and 1%-2% ethanol. The procedure yielded an iridescent maroon solid (4.6 mg, 0.0059 mmol, 37%). $^1$H NMR (500 MHz, DMSO-$d_6$) δ 8.14 (d, J=14.5 Hz, 2H), 8.16-8.01 (m, 6H), 7.67-7.54 (m, 8H), 7.03 (d, J=13.8 Hz, 2H), 6.59 (dd, J=8.9, 2.3 Hz, 2H), 6.47 (d, J=2.2 Hz, 2H), 4.10 (t, J=7.5 Hz, 8H), 2.80 (t, J=5.5 Hz, 4H), 2.43 (p, J=7.2 Hz, 4H), 1.88 (d, J=5.8 Hz, 2H). MS (ESI$^+$): calculated for $C_{46}H_{40}ClN_2O_2^+[M]^+$: 687.3; found: 687.0. Absorbance ($CH_2Cl_{12}$): 523 nm (ε=1.32±0.04×10$^4$ M$^{-1}$ cm$^{-1}$), 920 nm (ε=6.36±0.06×10$^4$ M$^{-1}$ cm$^{-1}$), 1029 nm (ε=2.07±0.01×10$^5$ M$^{-1}$ cm$^{-1}$). Emission ($CH_2Cl_{12}$, ex. 890 nm): 1059 nm.

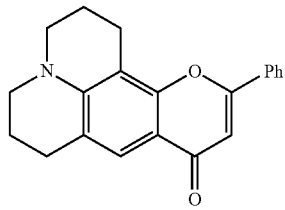 [SMILES: O=c1cc(-c2ccccc2)oc2c3c4c(cc12)CCCN4CCC3]

7-Julolidine-flavone (11-phenyl-2,3,6,7-tetrahydro-1H,5H,9H-pyrano[2,3-f]pyrido[3,2,1-ij]quinolin-9-one): 8-Hydroxyjulolidine (2,3,6,7-Tetrahydro-1H,5H-benzo[ij]quinolizin-8-ol) (749 mg, 3.96 mmol, 1.0 equiv.) and ethyl benzoyl acetate (1.20 mL, 6.93 mmol, 1.75 equiv.) were combined in a flame-dried 20 mL vial and heated at 180° C. for 48 h. The crude mixture was evaporated onto silica gel and purified by column chromatography with a 9:1 to 4:1 hexanes: ethyl acetate gradient, followed by chromatography with a 6:1 to 1:2 with 1% ethanol gradient. A beige solid (687.1 mg, 2.16 mmol, 55%) resulted. $^1$H NMR (500 MHz, Chloroform-d) δ 7.75 (dd, J=6.7, 3.0 Hz, 2H), 7.52 (s, 1H), 7.46-7.25 (m, 3H), 6.57 (s, 1H), 3.17 (dt, J=7.9, 5.5 Hz, 4H), 2.86 (t, J=6.5 Hz, 2H), 2.69 (t, J=6.3 Hz, 2H), 1.95 (p, J=6.3 Hz, 2H), 1.86 (p, J=6.2 Hz, 2H). $^{13}$C NMR (126 MHz, Chloroform-d) δ 177.59, 161.03, 153.58, 147.02, 132.38, 130.68, 128.74, 125.62, 122.08, 120.08, 112.67, 106.50, 105.52, 49.80, 49.29, 27.47, 21.29, 20.50, 20.48. MS (ESI$^+$): calculated for $C_{21}H_{20}NO_2^+[M+H]^+$: 318.2; found: 318.1. Absorbance ($CH_2Cl_{12}$): 283 nm, 381 nm.

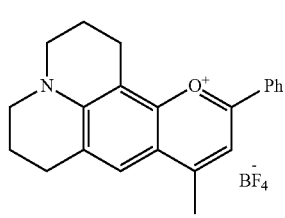

7-Julolidine-4-methyl-flavylium tetrafluoroborate (9-methyl-11-phenyl-2,3,6,7-tetrahydro-1H,5H-pyrano[2,3-f]pyrido[3,2,1-ij]quinolin-12-ium tetrafluoroborate): 7-Julolidine-flavone (118.4 mg, 0.373 mmol, 1.0 equiv.) was dissolved in THF (2 mL) in a 10 mL flame dried flask under $N_2$ atmosphere. The solution was cooled to 0° C. and methylmagnesium bromide (1.4 M in THF/toluene, 0.500 mL, 1.9 equiv.) was added dropwise. The reaction was warmed to rt and stirred for 17 h. The reaction mixture was poured over ice, extracted with dichloromethane after the addition of 5% $HBF_4$, dried with $MgSO_4$, decanted, and evaporated. The crude product was purified by precipitation and filtration in hot ethyl acetate to yield a dark purple solid (81.9 mg, 0.203 mmol, 54%). $^1$H NMR (500 MHz, Acetone-$d_6$) δ 8.37-8.25 (m, 2H), 7.98 (s, 1H), 7.93-7.85 (m, 1H), 7.79-7.61 (m, 3H), 3.73 (t, J=5.8 Hz, 4H), 3.20 (t, J=6.4 Hz, 2H), 3.07-3.01 (m, 2H), 2.21-2.14 (m, 2H), 2.15-2.06 (m, 2H). $^{13}$C NMR (126 MHz, Acetone-$d_6$) δ 163.78, 160.84, 154.63, 153.89, 134.30, 131.21, 130.59, 130.05, 128.13, 125.00, 119.18, 111.85, 105.83, 51.86, 51.38, 28.48, 21.03, 20.36, 20.01, 19.62. MS (ESI$^+$): calculated for $C_{22}H_{22}NO^+$

[M]$^+$: 316.2; found: 316.1. Absorbance (CH$_2$Cl$_{12}$): 250 nm, 301 nm, 341 nm, 533 nm. Emission (CH$_2$Cl$_{12}$, ex. 530 nm): 617 nm.

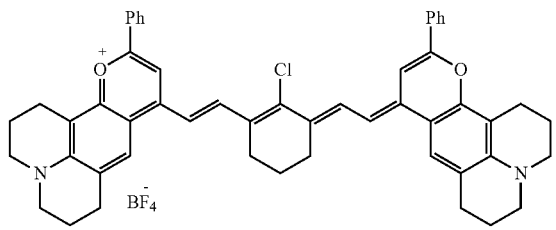

7-Julolidine flavylium heptamethine tetrafluoroborate (9-((E)-2-((E)-2-chloro-3-((E)-2-(11-phenyl-2,3,6,7-tetrahydro-1H,5H,9H-pyrano[2,3-f]pyrido[3,2,1-ij]quinolin-9-ylidene)ethylidene)cyclohex-1-en-1-yl)vinyl)-11-phenyl-2,3,6,7-tetrahydro-1H,5H-pyrano[2,3-f]pyrido[3,2,1-ij]quinolin-12-ium tetrafluoroborate): 7-Julolidine-4-methyl-flavylium tetrafluoroborate (40.1 mg, 0.099 mmol, 1.0 equiv.), N-[(3-(anilinomethylene)-2-chloro-1-cyclohexen-1-yl)methylene]aniline hydrochloride (17.5 mg, 0.049 mmol, 0.49 equiv.) and sodium acetate (12.4 mg, 0.151 mmol, 1.5 equiv.) were added to an oven-dried 20 mL vial, dissolved in ethanol (1 mL), freeze-pump-thawed ×3, and heated at 70° C. for 2 h. The crude product was dry loaded onto silica gel, and purified by column chromatography with a 9:1 dicholoromethane:acetone solvent mixture. The product was collected as a dark purple solid (15.4 mg, 0.018 mmol, 37%). $^1$H NMR (500 MHz, DMSO-d$_6$) δ 8.21-8.03 (m, 6H), 7.75 (s, 2H), 7.66-7.58 (m, 6H), 7.55 (s, 2H), 7.01 (d, J=13.9 Hz, 2H), 3.43-3.36 (m, 8H), 2.89 (t, J=6.4 Hz, 4H), 2.83 (t, J=6.0 Hz, 4H), 2.79 (t, J=6.3 Hz, 4H), 2.01-1.94 (m, 4H), 1.91 (d, J=6.0 Hz, 6H). MS (ESI$^+$): calculated for C$_{52}$H$_{48}$ClN$_2$O$_2^+$ [M]$^+$: 767.3, found: 767.3. Absorbance (CH$_2$Cl$_{12}$): 530 nm (ε=1.3±0.1×10$^4$ M$^{-1}$ cm$^{-1}$), 949 (ε=6.6±0.2×10$^4$ M$^{-1}$ cm$^{-1}$), 1061 nm (ε=2.38±0.07×10$^5$ M$^{-1}$ cm$^{-1}$). Emission (CH$_2$Cl$_{12}$, ex. 884 nm): 1089 nm.

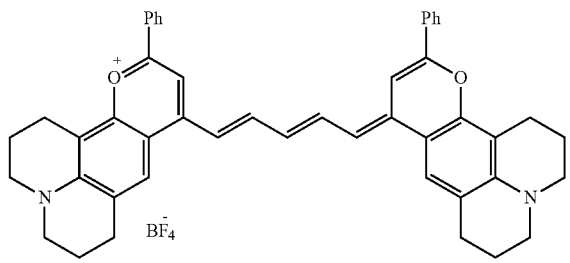

7-Julolidine flavylium pentamethine tetrafluoroborate (11-phenyl-9-((1E,3E,5E)-5-(11-phenyl-2,3,6,7-tetrahydro-1H,5H,9H-pyrano[2,3-f]pyrido[3,2,1-ij]quinolin-9-ylidene)penta-1,3-dien-1-yl)-2,3,6,7-tetrahydro-1H,5H-pyrano[2,3-f]pyrido[3,2,1-ij]quinolin-12-ium tetrafluoroborate): 7-Julolidine-4-methyl-flavylium tetrafluoroborate (50.0 mg, 0.124 mmol, 1.0 equiv.), malonaldehyde bis(phenylimine) mono hydrochloride (15.7 mg, 0.061 mmol, 0.49 equiv.) and sodium acetate (14.8 mg, 0.180 mmol, 1.5 equiv.) were added to an oven-dried 1 dram vial, dissolved in acetic anhydride (1.2 mL), freeze-pump-thawed ×3, and heated at 70° C. for 45 min. The crude product was evaporated onto silica gel and purified via column chromatography in dichloromethane with a 0.5% to 1.4% ethanol gradient. The product was isolated as a copper solid (9.4 mg, 0.012 mmol, 21%). $^1$H NMR (400 MHz, DMSO-d$_6$) δ 8.11 (d, J=13.0 Hz, 2H), 8.07-7.96 (m, 4H), 7.63-7.53 (m, 10H), 7.00 (d, J=13.4 Hz, 2H), 6.82-6.70 (m, 1H), 3.45-3.31 (m, 8H), 2.86 (t, J=6.4 Hz, 4H), 2.72 (t, J=6.3 Hz, 4H), 2.01-1.90 (m, 4H), 1.87 (d, J=6.2 Hz, 4H). MS (ESI$^+$): calculated for C$_{47}$H$_{43}$N$_2$O$_2^+$[M]$^+$: 667.3, found: 667.3. Absorbance (CH$_2$Cl$_{12}$): 588 nm (ε=1.6±0.1×10$^4$ M$^{-1}$ cm$^{-1}$), 806 nm (ε=5.1±0.3×10$^4$ M$^{-1}$ cm$^{-1}$), 897 nm (ε=2.5±0.1×10$^5$ M$^{-1}$ cm$^{-1}$). Emission (CH$_2$Cl$_{12}$, ex. 806 nm): 934 nm.

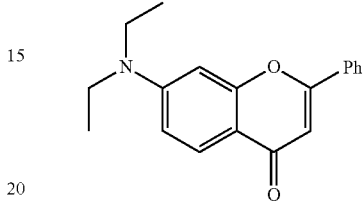

7-N,N-diethylamino-flavone (7-(diethylamino)-2-phenyl-4H-chromen-4-one): 3-diethylamino phenol (150.6 mg, 0.911 mmol, 1.0 equiv.) and ethyl benzoyl acetate (0.314 mL, 1.81 mmol, 2.0 equiv.) were added to a flame-dried 1 dram vial and heated to 100° C. for 5 h, followed by 180° C. for 15 h. The crude mixture was evaporated onto silica gel and purified by column chromatography in a 9:1, 6:1, and 3:1 hexanes:ethyl acetate gradient. The product was collected as a beige solid (135.8 mg, 0.463 mmol, 51%). $^1$H NMR (500 MHz, Chloroform-d) δ 7.96 (d, J=9.0 Hz, 1H), 7.87-7.80 (m, 2H), 7.46-7.39 (m, 3H), 6.66 (dd, J=9.1, 2.5 Hz, 1H), 6.62 (s, 1H), 6.49 (d, J=2.5 Hz, 1H), 3.38 (q, J=7.1 Hz, 4H), 1.18 (t, J=7.1 Hz, 6H). $^{13}$C NMR (126 MHz, Chloroform-d) δ 177.53, 161.94, 158.68, 151.92, 132.21, 130.91, 128.79, 126.64, 125.92, 113.06, 110.43, 107.11, 96.33, 44.67, 12.46. MS (ESI$^+$): calculated for C$_{19}$H$_{20}$NO$_2^+$ [M+H]$^+$: 294.2; found: 293.8. Absorbance (CH$_2$Cl$_{12}$): 233 nm, 275 nm, 365 nm. (See U.S. Pat. No. 5,919,950, which is fully incorporated by reference herein.)

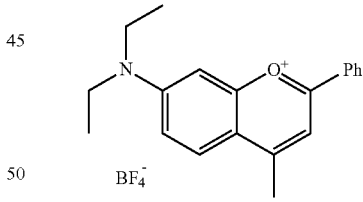

7-N,N-diethylamino-4-methyl-flavylium tetrafluoroborate (7-(dimethylamino)-4-methyl-2-phenylchromenylium tetrafluoroborate): 7-N,N-diethylamino-flavone (72.0 mg, 0.245 mmol, 1.0 equiv.) was dissolved in THF (2.4 mL) in a flame-dried 20 mL vial in an N$_2$ atmosphere. The solution was cooled to 0° C. and methylmagnesium bromide (1.1 M in THF/toluene, 0.540 mL, 2.4 equiv.) was added dropwise. The reaction was warmed to room temperature and stirred for 26 h. The reaction mixture was quenched with 5% HBF$_4$, poured over ice, and extracted with dichloromethane, dried with MgSO$_4$, filtered, and evaporated. The crude product was purified by precipitation in ethyl acetate to yield a dark red solid (48.1 mg, 0.137 mmol, 52%). $^1$H NMR (300 MHz, Acetone-d$_6$) δ 8.44-8.33 (m, 2H), 8.28 (d, J=9.6 Hz, 1H), 8.13 (s, 1H), 7.82-7.65 (m, 3H), 7.61 (dd, J=9.7, 2.6 Hz, 1H), 7.43 (d, J=2.6 Hz, 1H), 3.86 (q, J=7.1 Hz, 4H), 1.38 (t, J=7.1 Hz, 6H). $^{13}$C NMR (126 MHz, Acetone-d$_6$) δ 165.84, 164.62, 160.12, 157.44, 134.91, 130.62, 130.55, 130.03, 128.65, 119.22, 118.95, 112.74, 96.81, 46.75, 19.87, 12.80. MS (ESI$^+$): calculated for C$_{20}$H$_{22}$NO$^+$[M]$^+$: 292.2; found: 292.2. Absorbance (CH$_2$Cl$_{12}$): 239 nm, 295 nm, 338 nm, 514 nm. Emission (CH$_2$Cl$_{12}$, ex. 500 nm). 592 nm. (See U.S. Pat. No. 5,231,190, which is fully incorporated by reference herein.)

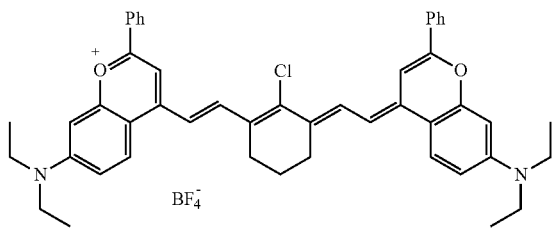

7-N,N-diethylamino flavylium heptamethine tetrafluoroborate (4-((E)-2-((E)-2-chloro-3-(2-((E)-7-(diethylamino)-2-phenyl-4H-chromen-4-ylidene)ethylidene)cyclohex-1-en-1-yl)vinyl)-7-(diethylamino)-2-phenylchromenylium tetrafluoroborate): 7-N,N-diethylamino-4-methyl-flavylium tetrafluoroborate (10.6 mg, 0.028 mmol, 1.0 equiv.), N-[(3-(anilinomethylene)-2-chloro-1-cyclohexen-1-yl)methylene]aniline hydrochloride (4.5 mg, 0.013 mmol, 0.45 equiv.), and sodium acetate (6.9 mg, 0.084 mmol, 3.0 equiv.) were added to a flame-dried 1 mL vial and dissolved in 0.30 mL of a 7:3 mixture of n-butanol:toluene. The mixture was freeze-pump-thawed ×3 and heated to 100° C. for 10 min. The crude product was purified by column chromatography in dichloromethane with a 0.5% to 6% ethanol solvent gradient to yield a purple solid (4.0 mg, 0.005 mmol 40%). $^1$H NMR (500 MHz, Acetonitrile-d$_3$) δ 8.04 (d, J=13.8 Hz, 2H), 7.86 (d, J=7.5 Hz, 4H), 7.62 (dd, J=9.8, 3.7 Hz, 2H), 7.54 (dt, J=26.9, 7.1 Hz, 6H), 7.18 (d, J=3.6 Hz, 2H), 6.70 (dd, J=13.8, 4.0 Hz, 2H), 6.66-6.59 (m, 2H), 6.40 (d, J=2.7 Hz, 2H), 3.37 (t, J=7.1 Hz, 8H), 2.74 (t, J=6.0 Hz, 4H), {peak at 1.9-2.0 ppm, beneath CD$_3$CN solvent peak, (m, 2H)}, 1.18 (t, J=6.9 Hz, 12H). MS (ESI$^+$): calculated for C$_{48}$H$_{48}$ClN$_2$O$_2$$^+$[M]$^+$: 719.3, found: 719.0. Absorbance (CH$_2$Cl$_{12}$): 524 nm (ε=1.1±0.1×10$^4$ M$^{-1}$ cm$^{-1}$), 923 nm (ε=4.4±0.4×10$^4$ M$^{-1}$ cm$^{-1}$), 1034 nm (ε=1.8±0.2×10$^5$ M$^{-1}$ cm$^{-1}$). Emission (CH$_2$Cl$_{12}$, ex. 890 nm): 1062 nm.

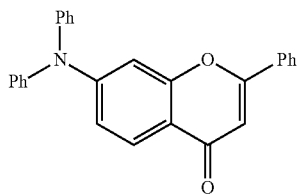 [SMILES: O=c1cc(-c2ccccc2)oc2cc(N(c3ccccc3)c3ccccc3)ccc12]

7-Diphenylamino-flavone (7-(diphenylamino)-2-phenyl-4H-chromen-4-one): 7-Trifluoromethanesulfonate-flavone (4-oxo-2-phenyl-4H-chromen-7-yl trifluoromethanesulfonate) (50.3 mg, 0.136 mmol, 1.0 equiv.), RuPhos-Pd-G3 (11.6 mg, 0.014 mmol, 0.1 equiv), RuPhos (6.4 mg, 0.014 mmol, 0.1 equiv.), and cesium carbonate (71.6 mg, 0.220 mmol, 1.6 equiv.) were added to a flame-dried 2-dram vial under a N$_2$ atmosphere and dissolved in THF (1.4 mL). The solution was heated at 50° C. for 13 h. The crude mixture was purified by column chromatography with a 20:1 to 15:1, 10:1, and 8:1 hexanes:ethyl acetate gradient to isolate a yellow solid (36.7 mg, 0.094 mmol, 69%). $^1$H NMR (400 MHz, Chloroform-d) δ 8.01 (d, J=8.9 Hz, 1H), 7.85 (dd, J=7.7, 2.0 Hz, 2H), 7.52-7.44 (m, 3H), 7.41-7.34 (m, 4H), 7.26-7.15 (m, 7H), 7.01 (dd, J=8.8, 2.3 Hz, 1H), 6.97 (d, J=2.2 Hz, 1H), 6.74 (s, 1H). $^{13}$C NMR (151 MHz, Chloroform-d) δ 177.72, 162.81, 157.83, 153.05, 146.22, 132.03, 129.91, 129.01, 126.47, 126.42, 126.22, 125.29, 107.59, 106.50. MS (ESI$^+$): calculated for C$_{27}$H$_{20}$NO$_2$$^+$[M+H]$^+$: 390.2, found: 390.2. Absorbance (CH$_2$Cl$_{12}$): 228 nm, 285 nm, 371 nm.

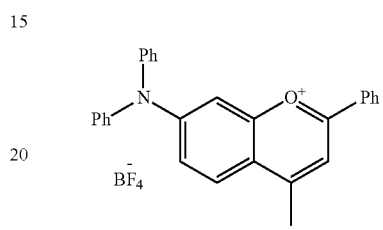

7-Diphenylamino-4-methyl-flavylium tetrafluoroborate (7-(diphenylamino)-4-methyl-2-phenylchromenylium tetrafluoroborate): 7-Diphenylamino-flavone (27.8 mg, 0.71 mmol, 1 equiv.) was added to a flame-dried 1 dram vial under a N$_2$ atmosphere, dissolved in THF (0.55 mL), and cooled to 0° C. Methylmagnesium bromide (1.04 M, 0.170 mL, 2.5 equiv.) was added dropwise, and the solution was warmed to rt and stirred for 8 h. The solution was quenched with 0.20 mL of 5% HBF$_4$ over ice, extracted with dichloromethane/water, dried with MgSO$_4$, filtered, and evaporated. The crude product was purified by precipitation in cold diethyl ether and filter to yield a dark purple solid (22.8 mg, 0.048 mmol, 67%). $^1$H NMR (500 MHz, Chloroform-d) δ 8.26-8.21 (m, 2H), 8.16 (s, 1H), 8.06 (d, J=9.5 Hz, 1H), 7.64 (t, J=7.4 Hz, 1H), 7.57 (t, J=7.7 Hz, 2H), 7.51 (t, J=7.8 Hz, 4H), 7.41 (t, J=7.5 Hz, 2H), 7.36-7.29 (m, 5H), 7.04 (d, J=2.3 Hz, 1H), 2.99 (s, 2H). $^{13}$C NMR (126 MHz, Chloroform-d) δ 167.98, 167.45, 158.64, 157.55, 143.42, 130.80, 130.01, 129.02, 128.89, 128.78, 128.38, 127.20, 121.70, 119.78, 114.66, 101.53, 20.52. MS (ESI$^+$): calculated for C$_{28}$H$_{22}$NO$^+$[M]$^+$: 388.2, found: 388.2. Absorbance (CH$_2$Cl$_{12}$): 249 nm, 288 nm, 351 nm, 528 nm.

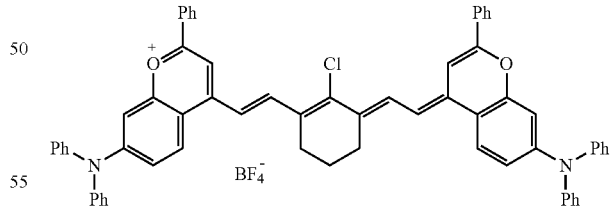

7-Diphenylamino flavylium heptamethine tetrafluoroborate (4-((E)-2-((E)-2-chloro-3-(2-((E)-7-(diphenylamino)-2-phenyl-4H-chromen-4-ylidene)ethylidene)cyclohex-1-en-1-yl)vinyl)-7-(diphenylamino)-2-phenylchromenylium tetrafluoroborate): 7-Diphenylamino-4-methyl-flavylium (5.00 mg, 0.011 mmol, 1.0 equiv.), N-[(3-(anilinomethylene)-2-chloro-1-cyclohexen-1-yl)methylene]aniline hydrochloride (1.73 mg, 0.0048 mmol, 0.46 equiv.), and 2,6-di-tert-butyl-4-methylpyridine (5.32 mg, 0.026 mmol, 2.5 equiv.) were added to a 1 mL vial under N$_2$ atmosphere and dissolved in 1,4 dioxane (0.30 mL). The solution was freeze-pump thawed ×3 and heated to 70° C., 80° C., and 90° C. for 10 min each. The crude product was purified by column chromatography (dry load), in dichloromethane with 0.5% ethanol to yield a purple solid (4.2 mg, 0.042 mmol, 88%). $^1$H NMR (500 MHz, Acetonitrile-d$_3$) δ 8.04-7.93 (m, 4H), 7.77 (d, J=6.9 Hz, 4H), 7.59-7.43 (m, 8H), 7.38 (t, J=7.6 Hz, 8H), 7.33-7.27 (m, 4H), 7.14 (s, 2H), 7.16-7.04 (m, 8H), 6.69 (s, 2H), 6.62 (d, J=2.2 Hz, 2H), 6.49-6.38 (m, 2H), 2.68 (m, 4H), {peak at 1.92-1.87 ppm, beneath CD$_3$CN solvent peak, (m, 2H)}. MS (ESI$^+$): calculated for C$_{64}$H$_{48}$ClN$_2$O$_2$$^+$[M]$^+$: 911.3, found: 910.8. Absorbance (CH$_2$Cl$_{12}$): 252 nm, 937 nm, 1047 nm. Emission (CH$_2$Cl$_{12}$, ex. 900 nm): 1079 nm.

flame-dried 25 mL Schlenk flask under N$_2$ atmosphere. n-Butanol (0.76 mL) and toluene (0.30 mL) were added and the solution was freeze-pump-thawed ×3. The reaction was heated to 105° C. for 15 min. The crude mixture was evaporated directly onto silica gel and purified by column chromatography with dichloromethane and 0.2 to 10% ethanol, followed by chromatography with dichloromethane and 1 to 5% ethanol. The product was isolated as a brown solid (4.1 mg, 0.005 mmol, 10%). NMR (500 MHz, DMSO-d$_6$) δ 8.81-6.64 (m, 28H), 3.00-2.80 (m, 4H), 2.02-1.87 (m, 2H). MS (ESI$^+$): calculated for C$_{48}$H$_{34}$ClO$^+$[M]$^+$: 677.2, found: 676.8. Absorbance (CH$_2$Cl$_{12}$): 436 nm, 519 nm, 891 nm, 998 nm. Emission (CH$_2$Cl$_{12}$, ex. 890 nm): 1024 nm.

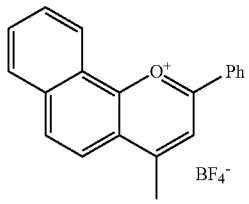

α-naptho-4-methyl flavylium tetrafluoroborate (4-methyl-2-phenylbenzo[h]chromen-1-ium tetrafluoroborate): α-napthoflavone (2-phenyl-4H-benzo[h]chromen-4-one) (201.4 mg, 0.740 mmol, 1.0 equiv.) was added to a flame-dried 50 mL 2 neck flask and dissolved in THF (7 mL) under a N$_2$ atmosphere and cooled to 0° C. Methylmagesium bromide (1.15 M, 1.6 mL, 2.5 equiv.) was added dropwise, the solution was warmed to room temperature and it was stirred overnight. The reaction was quenched with 4 mL of 5% HBF$_4$ and the resulting filtrate was filtered and rinsed with ethyl acetate to yield a lime green solid (242.9 mg, 0.678 mmol, 92%). $^1$H NMR (600 MHz, Acetonitrile-d$_3$) δ 9.10 (d, J=8.2 Hz, 1H), 8.72 (s, 1H), 8.63-8.55 (m, 2H), 8.34 (d, J=9.0 Hz, 1H), 8.28 (d, J=8.1 Hz, 1H), 8.23 (d, J=9.0 Hz, 1H), 8.14-8.09 (m, 1H), 8.05 (ddd, J=8.3, 7.0, 1.2 Hz, 1H), 7.94 (t, J=7.4 Hz, 1H), 7.84 (t, J=7.9 Hz, 2H), 3.20 (s, 3H). $^{13}$C NMR (126 MHz, Acetonitrile-d$_3$) δ 172.62, 171.15, 156.75, 138.38, 137.47, 134.72, 132.14, 131.37, 130.78, 130.57, 130.19, 129.88, 125.31, 124.71, 123.65, 121.44, 120.41, 22.16. MS (ESI$^+$): calculated for C$_{20}$H$_{15}$O$^+$[M]$^+$: 271.1, found: 270.6. Absorbance (CH$_3$CN): 210 nm, 230 nm, 314 nm, 379 nm, 429 nm. Emission (CH$_3$CN, ex. 425 nm): 530 nm.

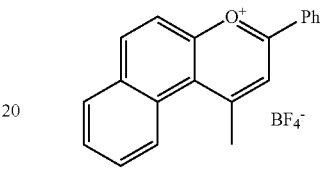

β-naptho-4-methyl-flavylium tetrafluoroborate (1-methyl-3-phenylbenzo[f]chromen-4-ium tetrafluoroborate): β-napthoflavone (3-phenyl-1H-benzo[f]chromen-1-one) (52.5 mg, 0.192 mmol, 1.0 equiv.) was dissolved in THF (1.8 mL) in a 15 mL 2 neck flask under N$_2$ atmosphere and cooled to 0° C. Methylmagnesium bromide (1.15 M, 0.40 mL, 2.4 equiv.) was added dropwise and the solution was warmed to rt and stirred overnight. The reaction was quenched with 2 mL 5% aqueous HBF$_4$ and the resulting filtrate was filtered rinsed with ethyl acetate to yield a bright yellow solid (23.2 mg, 0,065 mmol, 34%). $^1$H NMR (600 MHz, Acetonitrile-d$_3$) δ 9.03 (d, J=8.6 Hz, 1H), 8.79 (d, J=9.1 Hz, 1H), 8.70 (s, 1H), 8.58-8.49 (m, 2H), 8.35 (dd, J=7.9, 1.4 Hz, 1H), 8.27 (d, J=9.1 Hz, 1H), 8.09 (ddd, J=8.6, 7.0, 1.5 Hz, 1H), 8.01 (td, J=7.5, 7.0, 1.0 Hz, 1H), 7.93-7.86 (m, 1H), 7.80 (t, J=7.9 Hz, 2H), 3.54 (s, 3H). $^{13}$C NMR (126 MHz, Acetonitrile-d$_3$) δ 172.38, 169.17, 160.59, 144.47, 137.23, 133.49, 132.13, 132.00, 131.23, 130.73, 130.23, 129.35, 129.26, 129.01, 124.58, 121.92, 118.81, 29.03. MS (ESI$^+$): calculated for C$_{20}$H$_{15}$O$^+$[M]$^+$: 271.1, found: 270.8. Absorbance (CH$_3$CN): 211 nm, 240 nm, 298 nm, 433 nm. Emission (CH$_3$CN, ex. 400 nm): 507 nm.

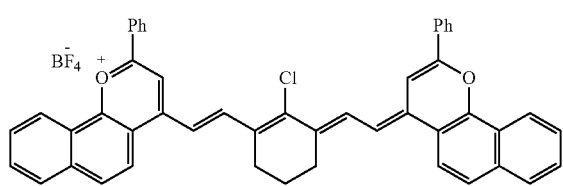

α-naptho-flavylium heptamethine tetrafluoroborate (4-((E)-2-((E)-2-chloro-3-((E)-2-(2-phenyl-4H-benzo chromen-4-ylidene)ethylidene)cyclohex-1-en-1-yl)vinyl)-2-phenylbenzo chromen-1-ium tetrafluoroborate): α-naptho-4-methyl flavylium tetrafluoroborate (40.1 mg, 0.112 mmol, 1.0 equiv.), N-[(3-(anilinomethylene)-2-chloro-1-cyclohexen-1-yl)methylene]aniline hydrochloride (19.6 mg, 0.055 mmol, 0.49 equiv.), and 2,6-di-tert-butyl-4-methylpyridine (60.9 mg, 0.297 mg, 2.7 equiv.) were added to a

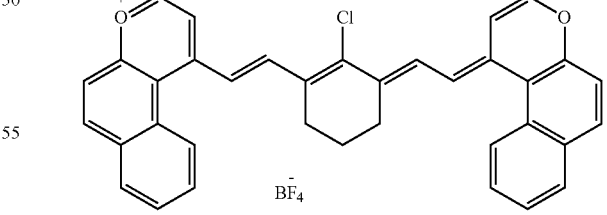

β-naptho-flavylium heptamethine tetrafluoroborate (1-((E)-2-((E)-2-chloro-3-((E)-2-(3-phenyl-1H-benzo[f] chromen-1-ylidene)ethylidene)cyclohex-1-en-1-yl)vinyl)-3-phenylbenzo[f]chromen-4-ium tetrafluoroborate): β-naptho-4-methyl-flavylium tetrafluoroborate (11.99 mg, 0.033 mmol, 1.0 equiv.), N-[(3-(anilinomethylene)-2-chloro-1-cyclohexen-1-yl)methylene]aniline hydrochloride (5.71 mg, 0.016 mmol, 0.47 equiv.), and 2,6-di-tert-butyl-4-methylpyridine (15.07 mg, 0.073 mmol, 2.19 equiv.) were added to a flame-dried 25 ml Schlenk flask under a $N_2$ atmosphere. The solution was freeze-pump-thawed ×3 and heated to 100° C. for 30 min. The crude mixture was purified by column chromatography in dichloromethane with a 0.5 to 0.7% ethanol gradient to yield a brown solid (1.8 mg, 0.003 mmol, 17%). MS (ESI$^+$): calculated for $C_{48}H_{34}ClO^+[M]^+$: 677.2, found: 676.8. Absorption ($CH_2Cl_{12}$): 1014 nm. Emission ($CH_2Cl_{12}$, ex. 880 nm): 1055 nm.

Example 5: Evaluation of Dyes

Polymethine dyes disclosed herein are characterized with respect to their photophysics including absorption, emission, extinction coefficient, quantum yields, and fluorescence lifetime. All quantum yields values obtained are absolute quantum yields values measured using an integrating sphere. Photostabilities are evaluated by sample irradiation with high powered LEDs. Additionally, solvatochromism, solvent compatibility, and stability are assessed.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

18. The compound of claim 1, wherein the compound is
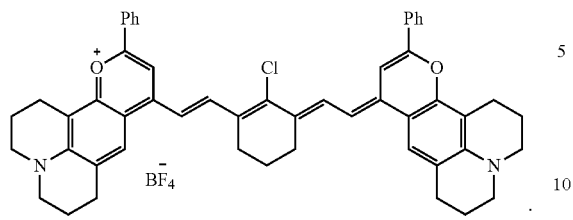

The invention claimed is:
1. A compound of formula I:

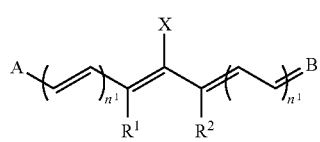

(I)

wherein:
A and B are independently selected from:

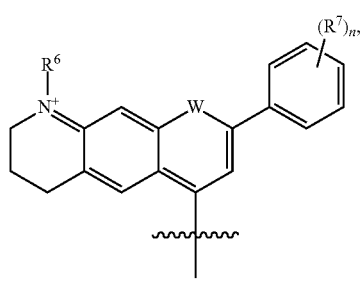

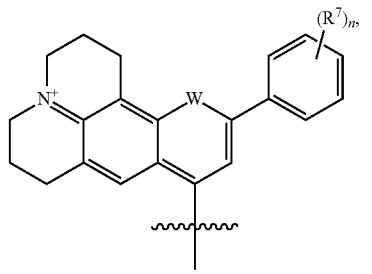

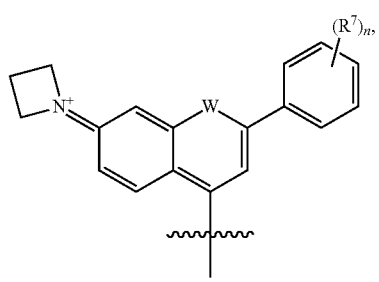

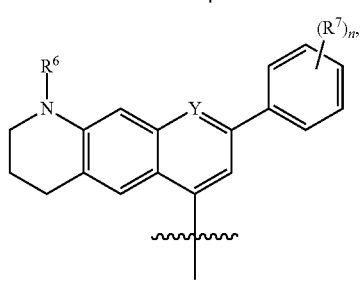

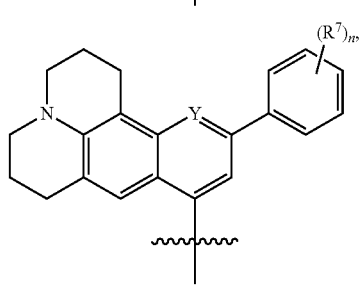

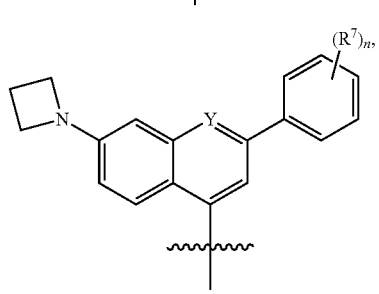

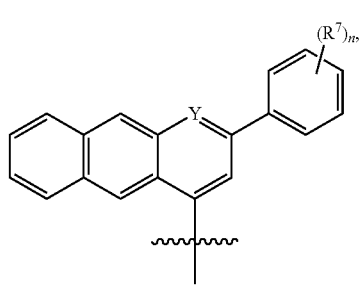

-continued

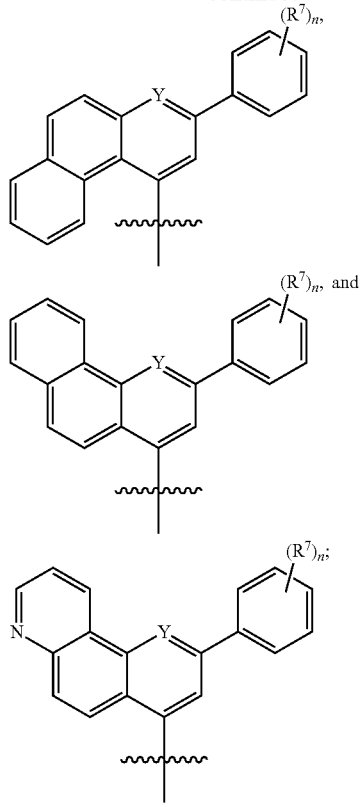

W is O;
Y is O⁺;
n is 0, 1, 2, 3, 4, or 5;
each instance of $R^6$ is independently selected from H, alkyl, fluoroalkyl, sulfonatoalkyl, acyl, cycloalkyl, heterocyclyl, aryl, and heteroaryl;
each instance of $R^7$ is independently selected from alkyl, alkoxy, acyl, cycloalkyl, heterocyclyl, aryl, heteroaryl, $N(R^6)R^6$, sulfonate, carbonate, cyano, ester, amide, and halo;
each instance of $n^1$ is 0 or 1;
X is H, halo or is Z—$R^4$—$N(R^5)$—C(O)O—$Y^1$;
Z is $N(R^3)$ or S;
$R^1$ and $R^2$ are independently selected from H and alkyl; or $R^1$ and $R^2$ together complete a cycloalkenyl ring, a heterocyclyl ring, or a polycyclyl ring system;
$R^3$, $R^4$, and $R^5$ are independently selected from alkyl; and
$Y^1$ is a cargo moiety.

2. The compound of claim 1, wherein at least one of A and B is not:

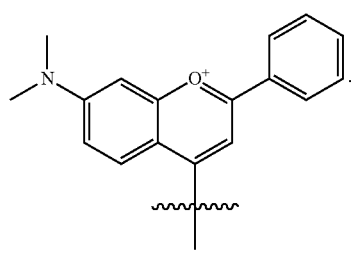 [SMILES: *c1cc(-c2ccccc2)[o+]c2cc(N(C)C)ccc12]

3. The compound of claim 1, wherein the compound is a compound of formula II:

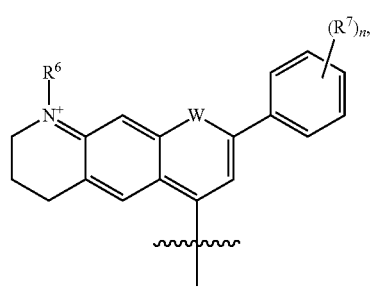

4. The compound of claim 1, wherein $R^1$ and $R^2$ together complete a cycloalkenyl ring.

5. The compound of claim 1, wherein $R^7$ is selected from haloalkyl, cyano, sulfonate, sulfonatoalkyl, sulfonatoalkyloxy, carboxyl, ester, amide, halo, nitro, alkylammonium, amine oxide, and haloalkyl.

6. The compound of claim 4, wherein at least one $R^7$ is selected from fluoroalkyl.

7. The compound of claim 4, wherein at least one $R^7$ is $(CH_2)_3C_6F_{13}$.

8. The compound of claim 1, wherein:
A and B are independently selected from:

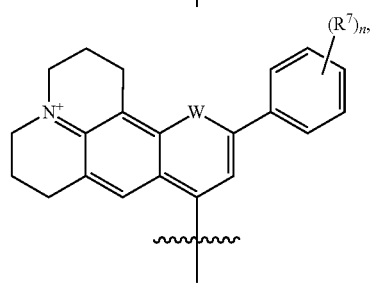

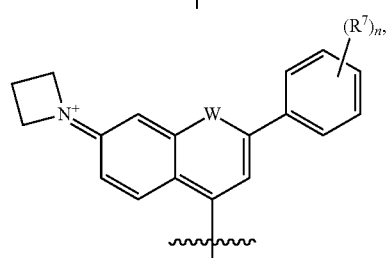

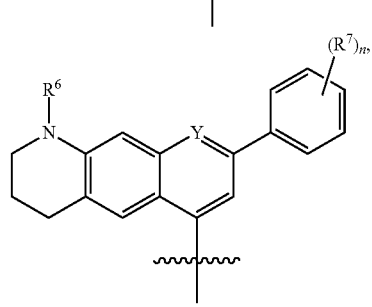

-continued

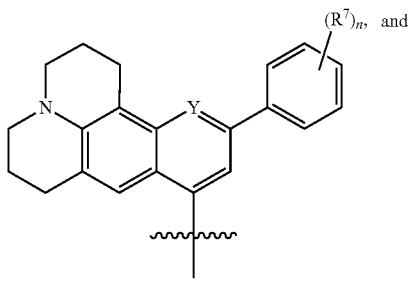

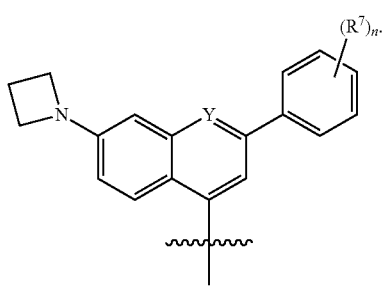

9. The compound of claim 1, wherein n is 0.

10. The compound of claim 1, wherein X is halo or Z—R⁴—N(R⁵)—C(O)O—Y; and R⁴ and R⁵ are independently selected from alkyl.

11. The compound of claim 1, wherein at least one of A and B is

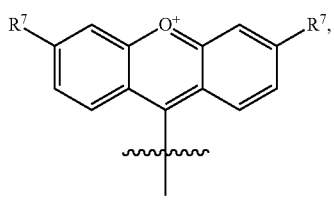

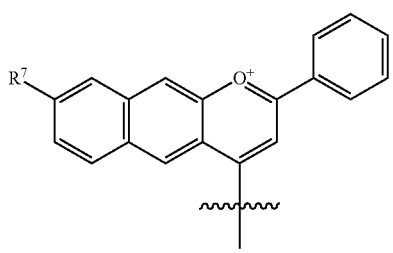,

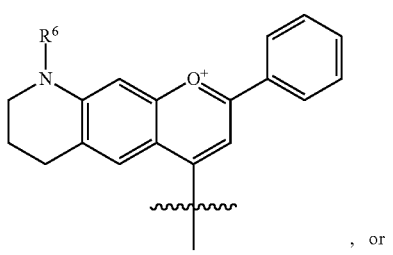, or

-continued

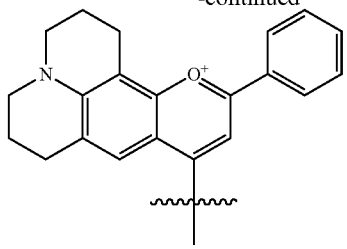

12. The compound of claim 1, wherein at least one of A and B is substituted with N(R⁸)R⁹, wherein R⁸ is cycloalkyl, heterocyclyl, aryl, or heteroaryl, and R⁹ is selected from H, alkyl, acyl, cycloalkyl, heterocyclyl, aryl, and heteroaryl; or wherein R⁸ and R⁹ together complete a heterocyclyl.

13. The compound of claim 1, wherein at least one of A and B is substituted with a 4-8 member N-linked heteroaryl or heterocyclyl.

14. The compound of claim 1, wherein at least one of A and B is substituted with sulfate, sulfonate, sulfonatoalkyl, or carboxylate.

15. A pharmaceutical composition comprising a compound of claim 1 and at least one pharmaceutically acceptable excipient.

16. A method of obtaining an image comprising:
illuminating a compound of claim 1 with excitation light, thereby causing the compound to emit fluorescence; and
detecting the fluorescence.

17. A method of preparing a compound of claim 1 comprising:
providing a starting material compound of formula I wherein A and B are the same:

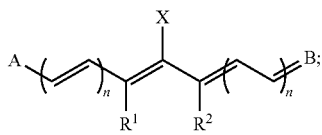

contacting the starting material compound with a basic amine, thereby producing a half-dye intermediate;
providing a compound of formula (IV):

$$R^8\text{-D} \quad \quad (IV);\text{ and}$$

contacting the half-dye intermediate with the compound of formula (IV), thereby producing the compound;
wherein:
A and B are independently selected from a bicyclic, tricyclic, and tetracyclic heteroaryl;
A and B are different;
each instance of n is 0 or 1;
X is H, halo or is Z—R⁴—N(R⁵)—C(O)O—Y¹;
Z is N(R³) or S;
R¹ and R² are independently selected from H and alkyl; or R¹ and R² together complete a cycloalkenyl ring, a heterocyclyl ring, or a polycyclyl ring system;
R³, R⁴, and R⁵ are independently selected from alkyl;
R⁸ is alkyl; and
Y¹ is a cargo moiety.